United States Patent
Chi et al.

(10) Patent No.: US 11,474,093 B2
(45) Date of Patent: Oct. 18, 2022

(54) ANALYSIS METHOD OF PROTEIN-PROTEIN INTERACTION AND A SCREENING METHOD OF PROTEIN-PROTEIN INTERACTION INHIBITORS USING A NANOPORE

(71) Applicants: Korea Research Institute of Bioscience and Biotechnology, Daejeon (KR); Seoul National University R&DB Foundation, Seoul (KR)

(72) Inventors: Seung Wook Chi, Daejeon (KR); Ki Bum Kim, Seoul (KR); Dong Kyu Kwak, Daejeon (KR); Mi Kyung Lee, Daejeon (KR); Hong Sik Chae, Seoul (KR); Ji Hyang Ha, Daejeon (KR)

(73) Assignees: Korea Research Institute of Bioscience and Biotechnology, Daejeon (KR); Seoul National University R&DB Foundation, Seoul (KR)

(*) Notice: Subject to any disclaimer, the term of this patent is extended or adjusted under 35 U.S.C. 154(b) by 232 days.

(21) Appl. No.: 16/043,980

(22) Filed: Jul. 24, 2018

(65) Prior Publication Data
US 2019/0162713 A1 May 30, 2019

Related U.S. Application Data

(63) Continuation-in-part of application No. PCT/KR2016/001113, filed on Feb. 2, 2016.

(30) Foreign Application Priority Data

Jan. 26, 2016 (KR) .................... 10-2016-0009577

(51) Int. Cl.
*G01N 33/487* (2006.01)
*G01N 27/04* (2006.01)
(Continued)

(52) U.S. Cl.
CPC ......... *G01N 33/48721* (2013.01); *C12Q 1/48* (2013.01); *G01N 27/04* (2013.01);
(Continued)

(58) Field of Classification Search
CPC ......... G01N 33/48721; G01N 27/3278; G01N 27/04; B82Y 5/00; B82Y 15/00
See application file for complete search history.

(56) References Cited

U.S. PATENT DOCUMENTS

2013/0071837 A1* 3/2013 Winters-Hilt ........ C12Q 1/6869
435/6.11
2016/0169864 A1* 6/2016 Grinstaff ................ B05D 1/007
204/452
2018/0362594 A1* 12/2018 Cech ........................ C12Q 1/68

FOREIGN PATENT DOCUMENTS

KR    10-2014-0046471    4/2014
WO    WO 2012/066075    5/2012

OTHER PUBLICATIONS

Han et al. (Anal. Chem. 2008 vol. 80, p. 4651-4658). (Year: 2008).*
(Continued)

*Primary Examiner* — Changhwa J Cheu
(74) *Attorney, Agent, or Firm* — John P. White

(57) ABSTRACT

The present invention relates to a method for screening protein-protein interaction inhibitors using a nanopore, a method for analyzing protein structures, a method for analyzing protein-protein interactions, and a kit therefor.

11 Claims, 10 Drawing Sheets

(51) Int. Cl.
   *G01N 33/66*    (2006.01)
   *B82Y 5/00*     (2011.01)
   *B82Y 15/00*    (2011.01)
   *C12Q 1/48*     (2006.01)
   *G01N 27/327*   (2006.01)
(52) U.S. Cl.
   CPC ....... *G01N 27/3278* (2013.01); *G01N 33/487* (2013.01); *G01N 33/66* (2013.01); *B82Y 5/00* (2013.01); *B82Y 15/00* (2013.01); *C12Y 205/01018* (2013.01)

(56) References Cited

OTHER PUBLICATIONS

Winters-Hilt et al. (BMC Bioinformatics 2007 vol. 8, S20). (Year: 2007).*

Sivaraman et al. (Protein Science 2013 vol. 22, p. 153-167). (Year: 2013).*

Harrington et al. Angew Chem 2015 127: 8272-8277 (Year: 2015).*

Jae-Sun Shin et al., "Structural convergence of unstructured p53 family transactivation domains in MDM2 recognition", Cell Cycle, 14:4, 533-543.

Wade M. Borcherds et al., "Evolution of Structure and Dynamics for a Family of Disordered Proteins", Biophysical Journal, 2011, vol. 110, No. 3, pp. 519a.

Yijun Huang et al., "Exhaustive Fluorine Scanning toward Potent p53-Mdm2 Antagonists", ChemMedChem 2012, 7, 49-52.

Michal Bista et al., "Transient Protein States in Designing Inhibitors of the MDM2-p53 Interaction", Structure, 2013, vol. 21, pp. 2143-2151.

Wilhelm J. Ansorge, "Next-generation DNA sequencing techniques", New Biotechnology, 2009, vol. 25, Issue 4, pp. 195-203.

* cited by examiner

[Fig. 1]
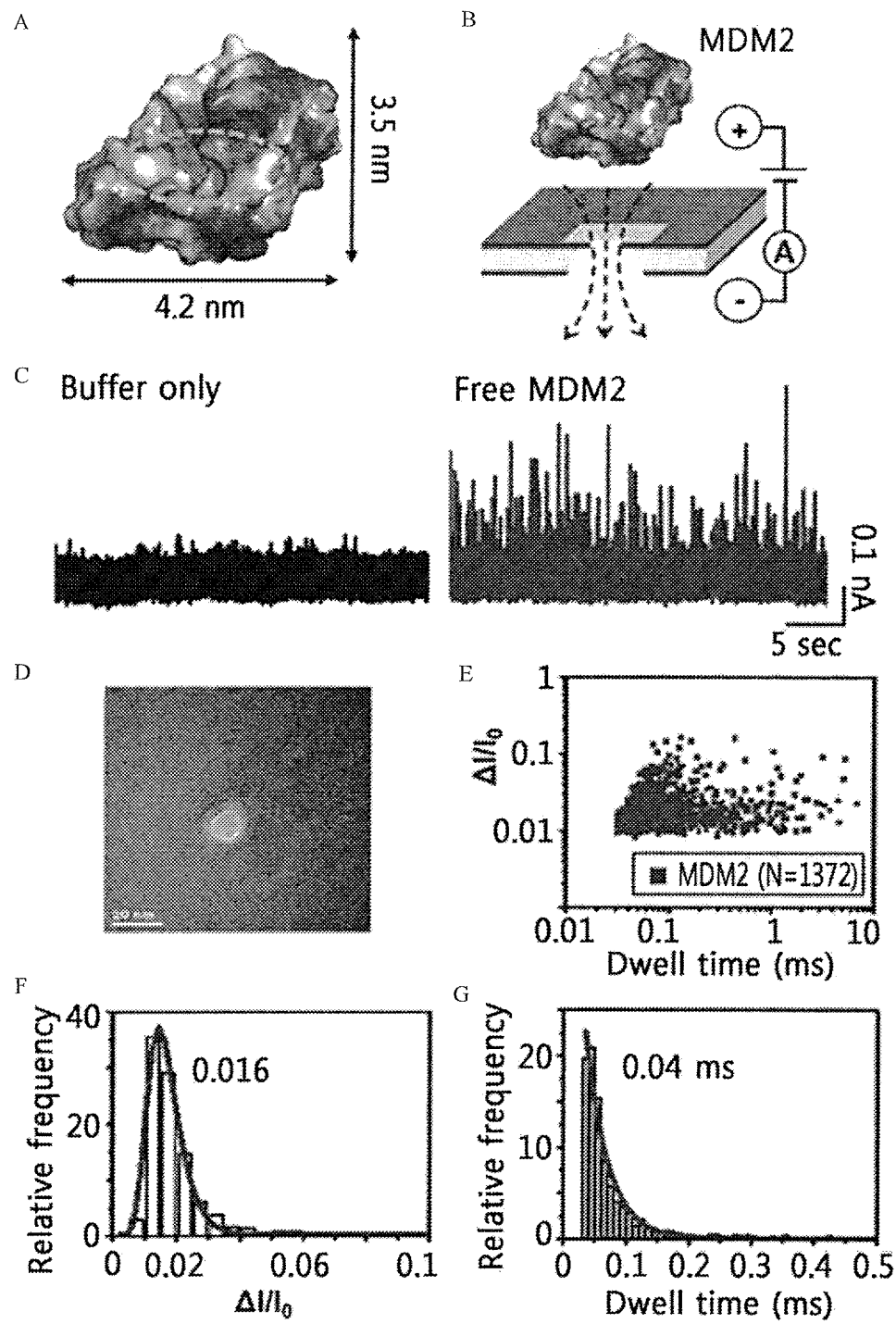

[Fig. 2]
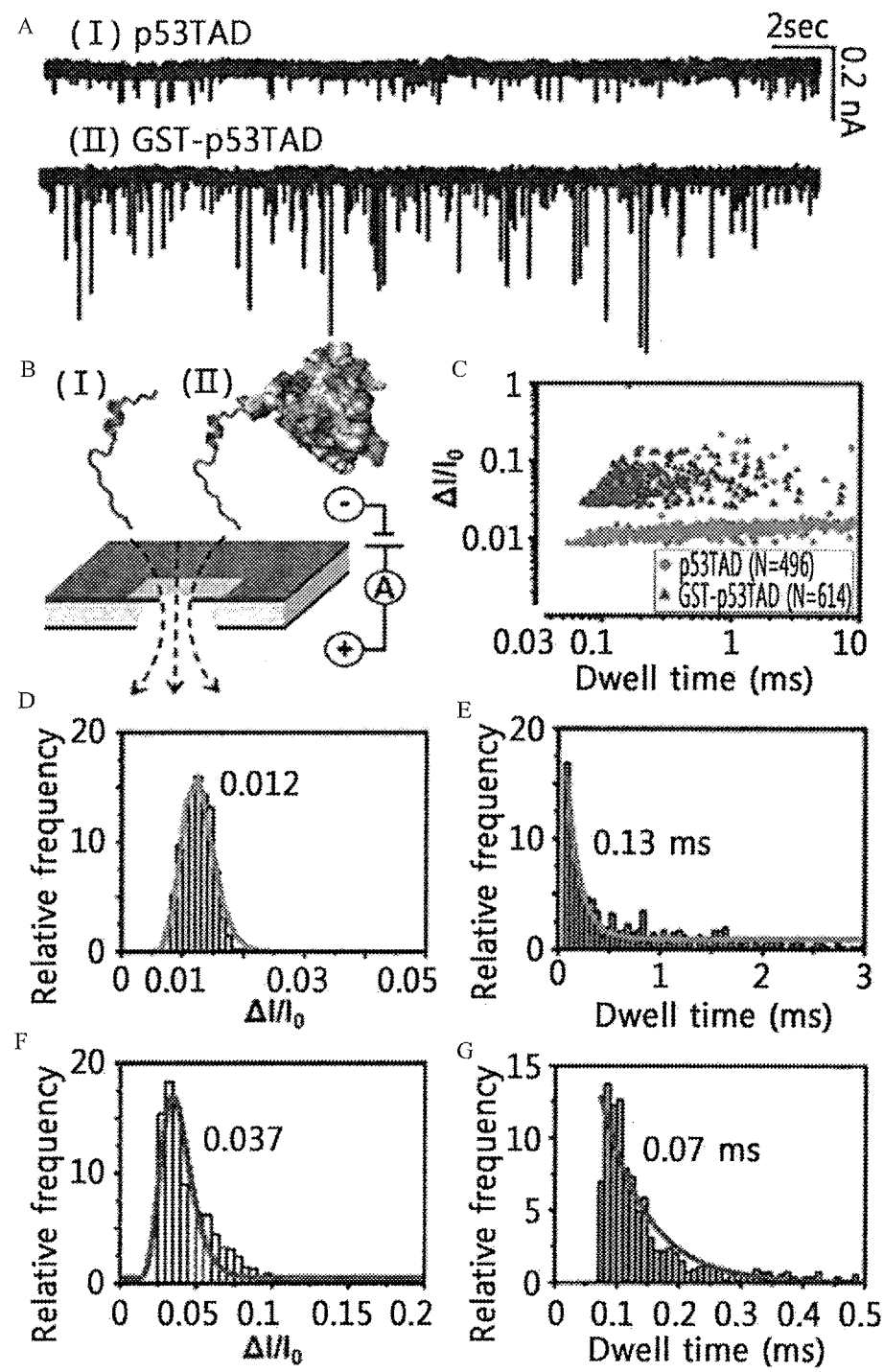

[Fig. 3]
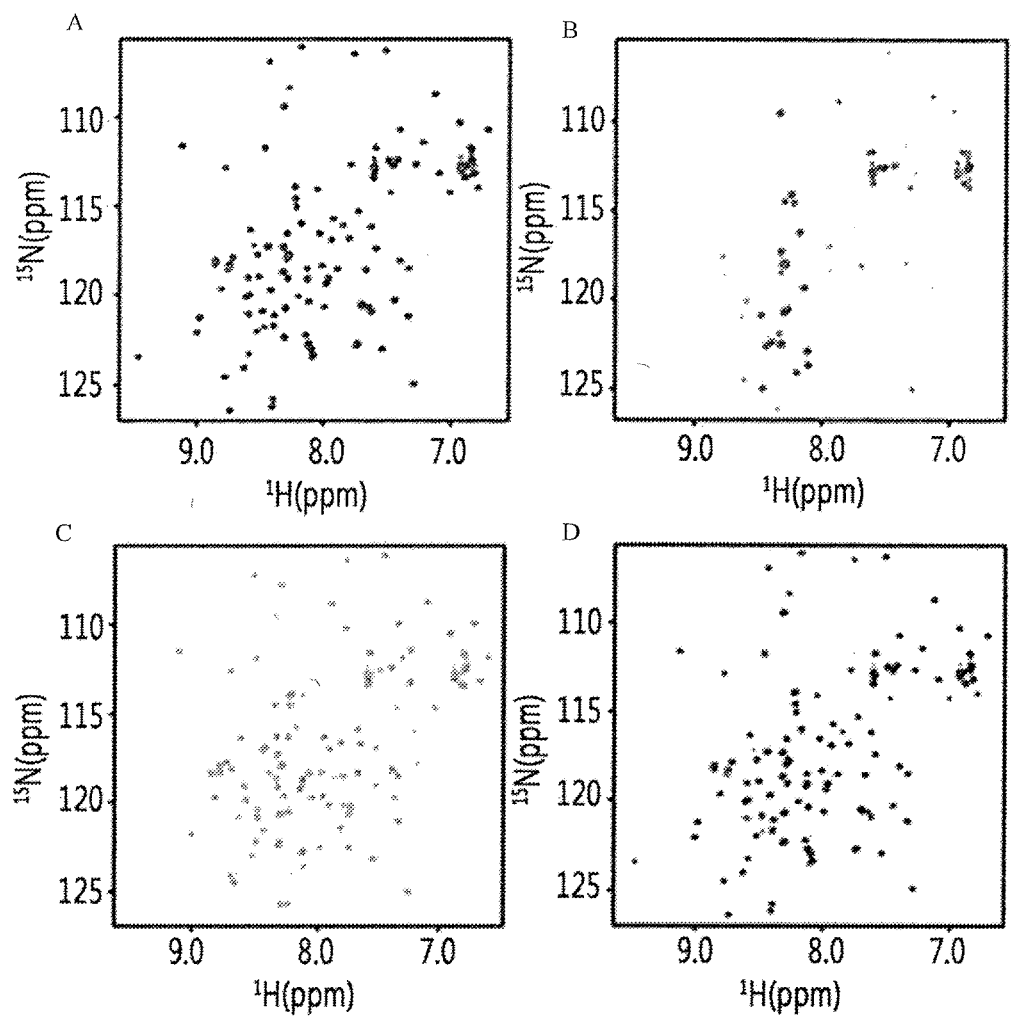

[Fig. 4]
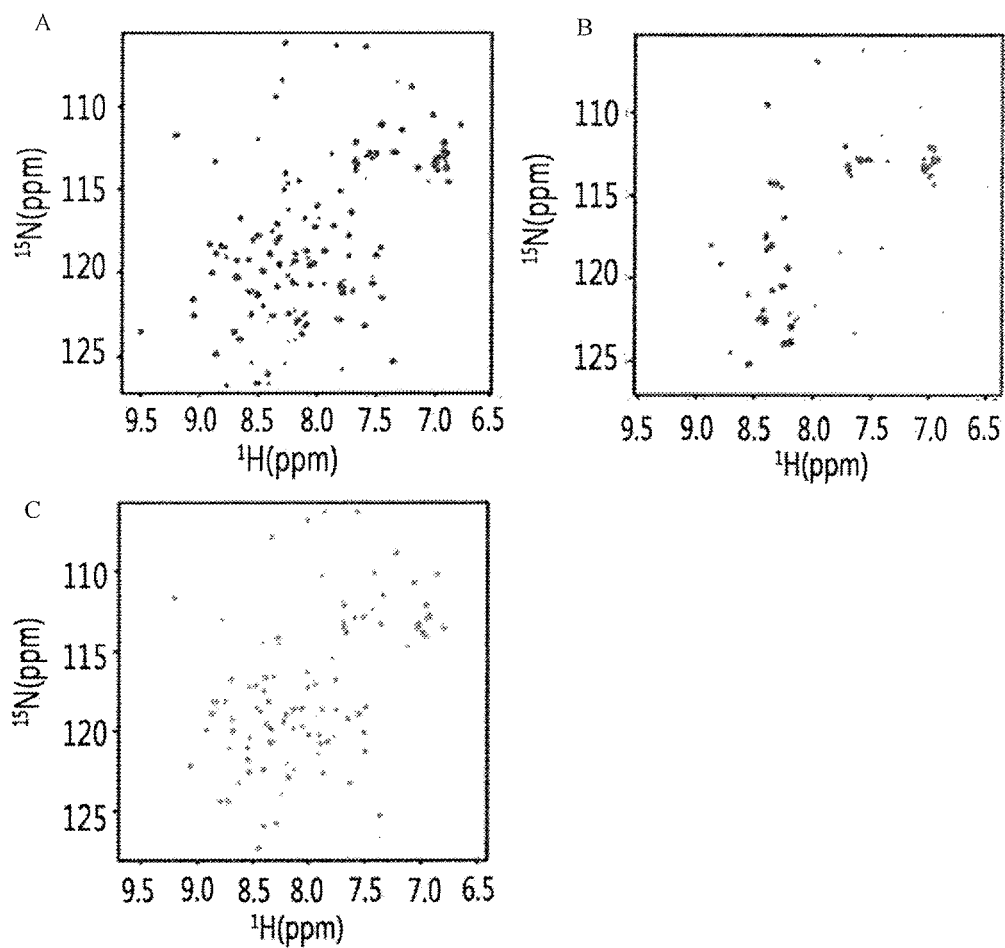

[Fig. 5]
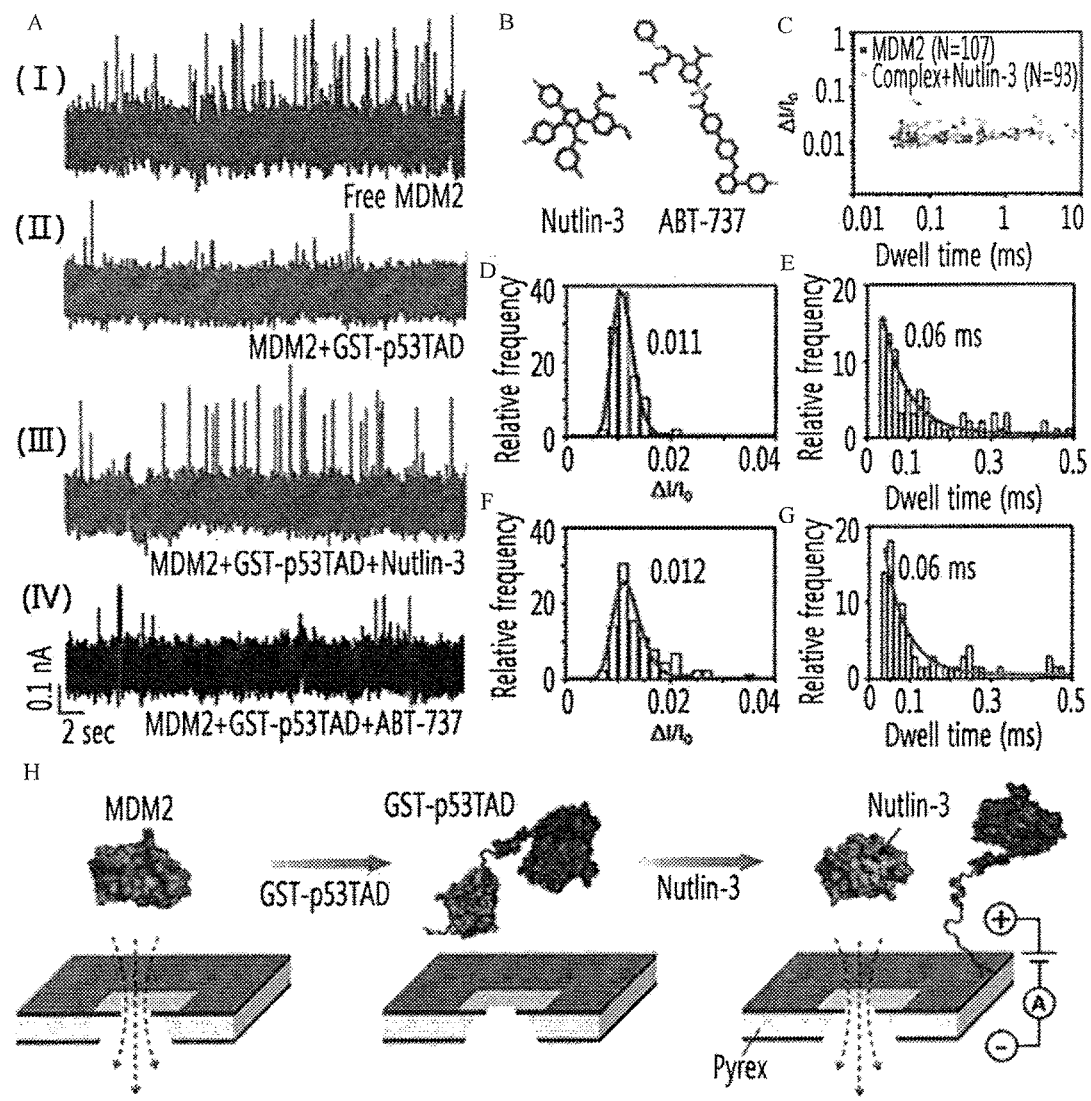

[Fig. 6]
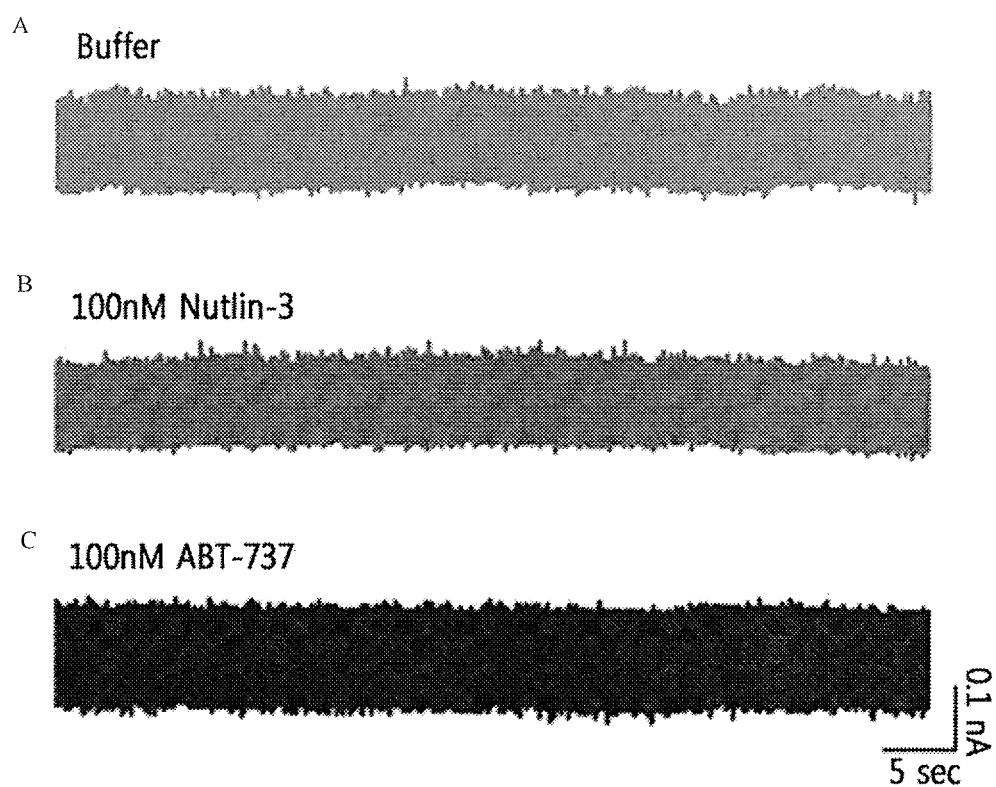

[Fig. 7]
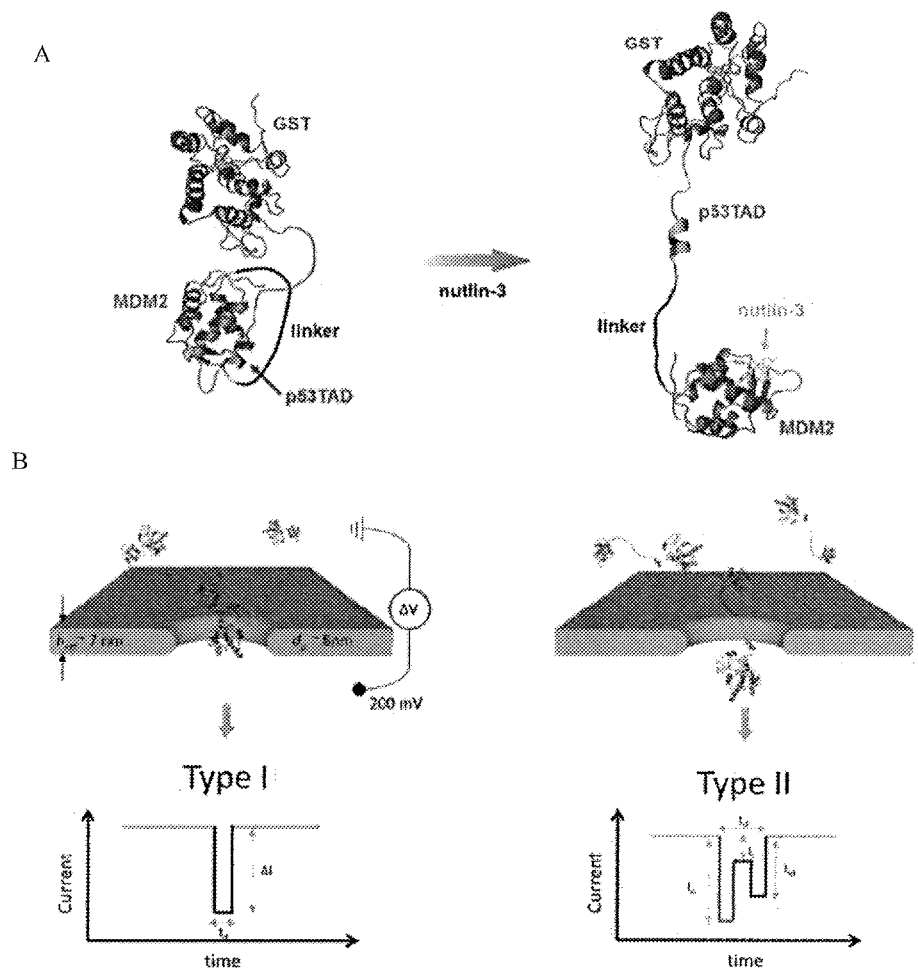

[Fig. 8]
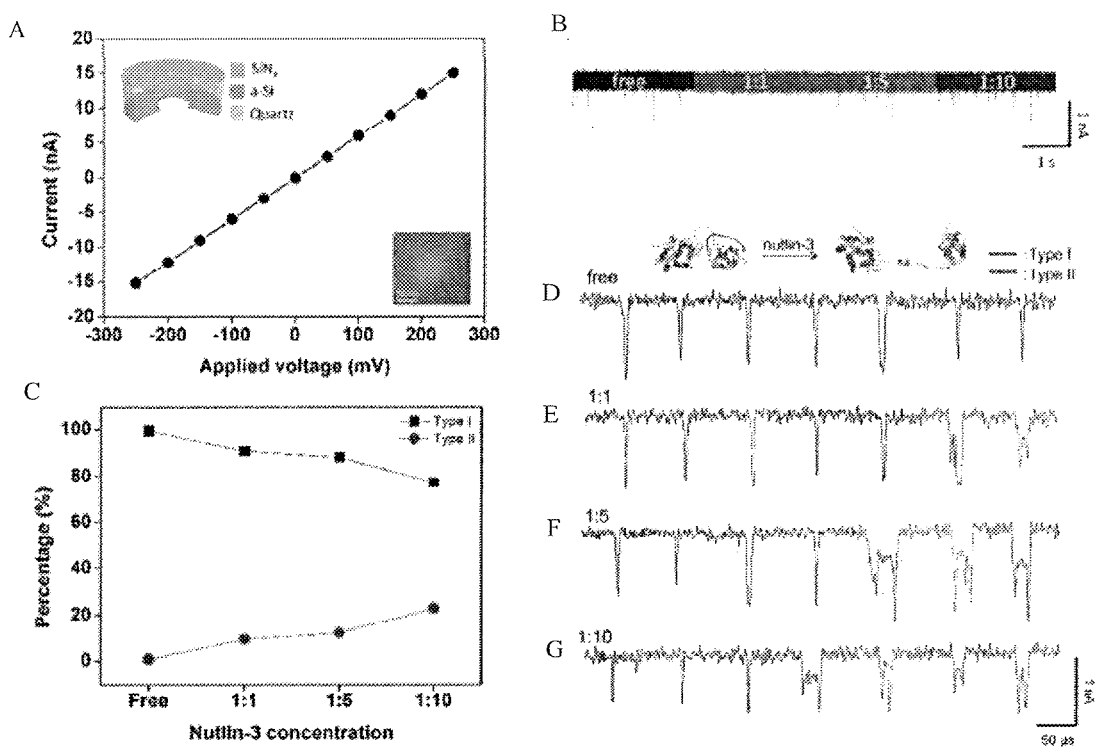

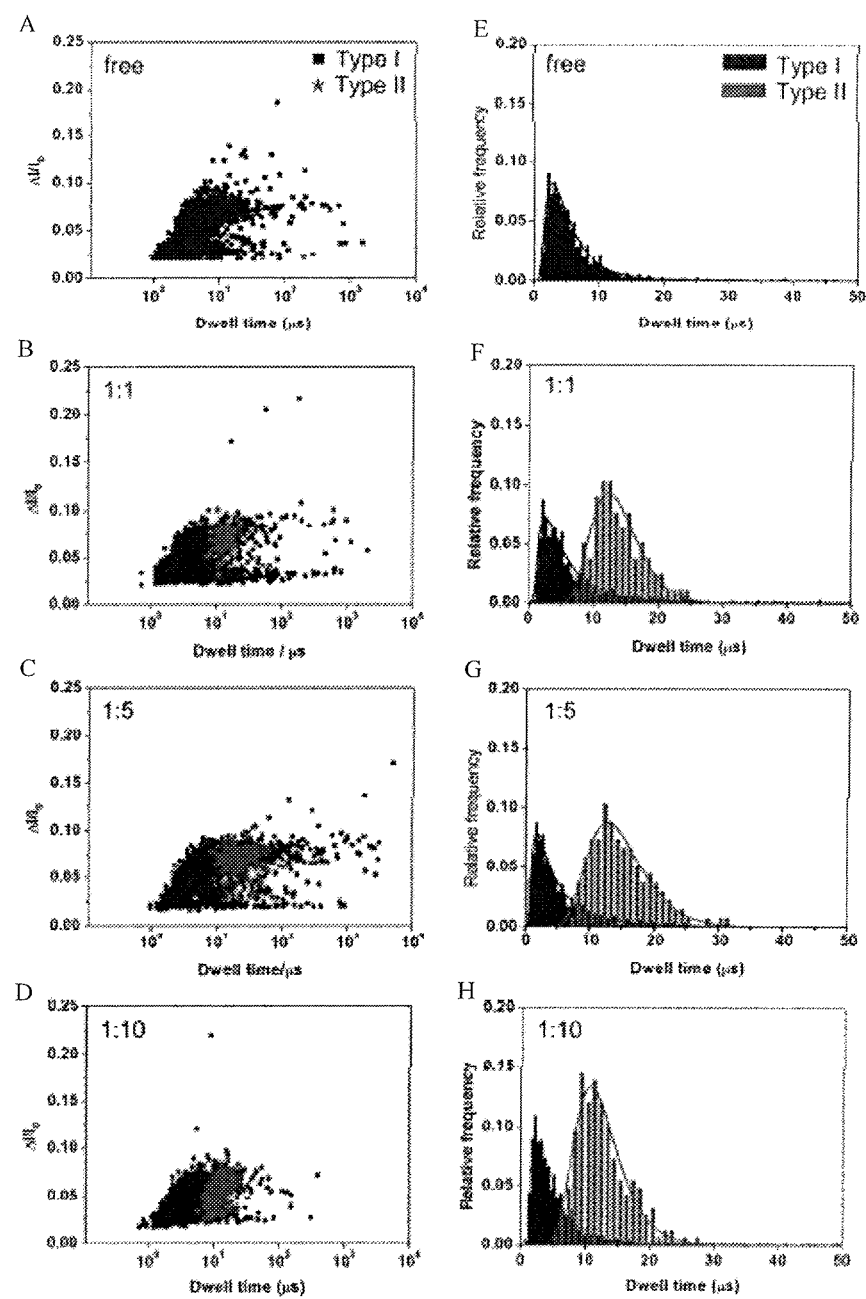
[Fig. 9]

[Fig. 10]
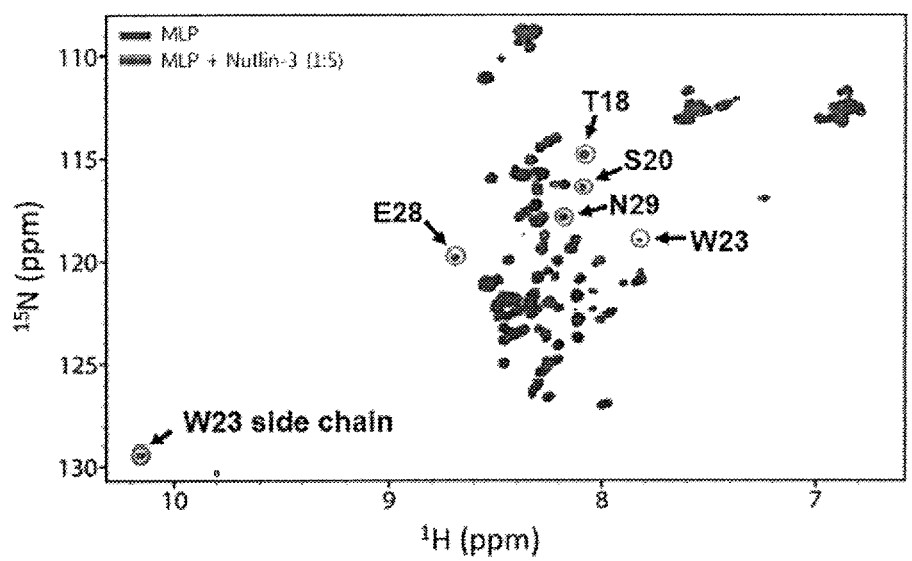
[Fig. 11]
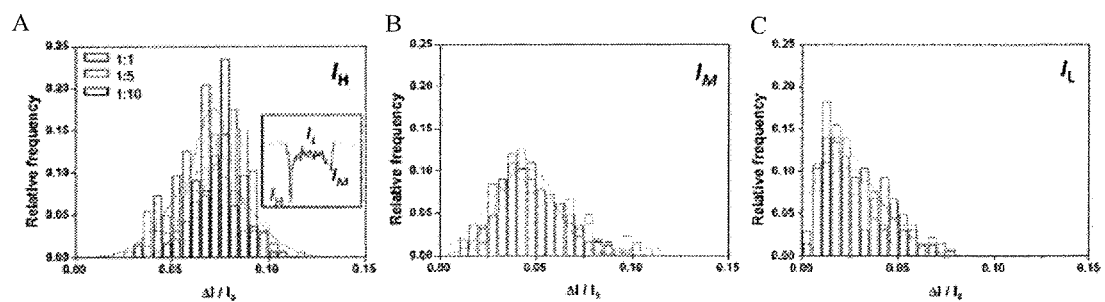

ANALYSIS METHOD OF PROTEIN-PROTEIN INTERACTION AND A SCREENING METHOD OF PROTEIN-PROTEIN INTERACTION INHIBITORS USING A NANOPORE

TECHNICAL FIELD

The present invention relates to a method for screening protein-protein interaction inhibitors, comprising comparing the electrical signal generated while a protein complex passes through a nanopore and the electrical signal generated while the protein complex treated with a protein-protein interaction inhibitor candidate passes through the nanopore, and determining the candidate as a protein-protein interaction inhibitor when there is an increase or decrease of signals.

Additionally, the present invention relates to a method for analyzing the structure of an interacting protein using a nanopore, comprising measuring the electrical signal generated while a protein or protein complex passes through the nanopore.

Additionally, the present invention relates to a method for analyzing a protein-protein interaction using a nanopore, which comprises comparing the electrical signal generated while a first protein or second protein passes through a nanopore and the electrical signal generated while a protein complex, which is formed by binding between the first protein and the second protein through a protein-protein interaction, passes through the nanopore.

BACKGROUND ART

In finding drugs, a protein-protein interaction (PPI) is a target for effective disease treatment; however, methods for screening PPI inhibitors through high-throughput screening have not yet been commercialized.

Nanopores, buried in a thin insulating film, generally function as the only pipe facilitating the flow of ionic current between two fluid reservoirs. Experiments on the nanopores based on the principle of a macroscale Coulter counter are related to changes in the ionic current. When the ionic current is electrophoretically induced through the nanopores in the presence of an external electric field, the length, size, charge, and form of electrically charged biomolecules are determined.

Protein nanopores such as α-hemolysin generally provide properties of high sensitivity and low noise, while the lipid bilayer that supports the same is weak and has constraints in using the protein nanopores due to the fixed size. Meanwhile, solid-state nanopores are generally formed on an insulating thin film (thickness of 10 nm to 50 nm) such as silicon nitride film and silicon oxide film in various sizes. They can easily be integrated using the wafer scale technology, and can be applied to broader experimental conditions due to their firmness.

Biomolecule analysis technology using the nanopores is advantageous in that it enables degradation at the single-molecule level as well as high-sensitivity, label-free, and real-time detection, etc., thereby facilitating active development of the screening technology using nanopores.

Techniques of using such nanopores have been used to investigate physiological properties of various biomolecules such as DNA, RNA, and proteins; and in particular, nanopore-applied DNA sequencing has been reported (Ansorge W J, *N Biotechnol.* 2009 April; 25(4):195 to 203).

However, it has not been revealed yet that the nanopores could be used in the screening of small molecule drugs such as PPI inhibitors.

DISCLOSURE

Technical Problem

The present inventors have made extensive efforts to develop accurate and effective methods for screening protein-protein interaction inhibitors using picomoles of samples, and as a result, found out that nanopores can be used to screen protein-protein interaction inhibitors by measuring changes in the electrical signals of the nanopores, thereby completing the present invention.

Technical Solution

An object of the present invention is to provide a method for screening protein-protein interaction inhibitors using a nanopore, comprising: (a) forming a protein complex in which a first protein and a second protein are bound by a protein-protein interaction; (b) measuring the electrical signal generated while the protein complex passes through the nanopore; and (c) treating the protein complex with a protein-protein interaction inhibitor candidate, and measuring the intensity of an electrical signal generated while the protein complex passes through the nanopore.

Another object of the present invention is to provide a method for analyzing the structure of an interacting protein using a nanopore, comprising measuring the electrical signal generated while a protein or protein complex passes through the nanopore.

Still another object of the present invention is to provide a method for analyzing a protein-protein interaction using a nanopore, comprising: (a) passing a first protein or second protein through a nanopore; and measuring the electrical signal generated therefrom; (b) forming a protein complex in which the first protein and the second protein are bound by a protein-protein interaction; and measuring the electrical signal generated while the protein complex passes through the nanopore; and (c) comparing the electrical signals generated in (a) and (b).

Advantageous Effects

Protein binding inhibitors can be effectively screened even in a picomole amount using the method of the present invention for screening protein-protein interaction inhibitors. The protein binding inhibitors discovered, which target a particular protein binding, can be used in the treatment of a disease related to the protein-protein interaction, and particularly effectively in discovering an anti-cancer drug.

BRIEF DESCRIPTION OF THE DRAWINGS

FIG. 1 shows diagrams illustrating the results of nanopore-based analysis of MDM2 translocation events. FIG. 1A shows the surface of the structure of a free MDM2 N-terminal domain (PDB code: 1YCR). Negatively and positively charged residues are indicated in red and blue, respectively. The p53TAD-binding pocket in MDM2 is indicated by the yellow dotted circle. FIG. 1B shows a schematic diagram illustrating the MDM2 translocation. The positively charged MDM2 passes through nanopores by a negatively applied voltage of −175 mV. FIG. 1C shows the results of measured blockade current of 100 nM MDM2 that passes through nanopores in 1 M KCl and 1×PBS (pH 7.4). FIG. 1D shows a TEM image of a nanopore having a diameter of about 10 nm. FIG. 1E shows a graph illustrating the scatter plot of MDM2 translocation events. FIGS. 1F and 1G show histograms illustrating normalized current drop ($\Delta I/I_0$) and the dwell time of MDM2 translocation events, respectively, which were fitted to the single exponential decay function and resulted in mean values of about 0.016 ms and 0.04 ms, respectively.

FIG. 2 shows the results of nanopore-based analysis of p53TAD and GST-p53TAD translocation events. FIG. 2A shows the results of the measured current of p53TAD and GST-p53TAD translocations, which were generated while p53TAD (I) and GST-p53TAD (II) passed through nanopores, at the applied voltage of +100 mV. FIG. 2B shows a schematic diagram illustrating the p53TAD (I) and GST-p53TAD (II) translocation events, and FIG. 2C shows a graph illustrating the scatter plot of p53TAD (I) and GST-p53TAD (II) translocation events. The p53TAD and GST-p53TAD translocation events are indicated as yellow circles and red triangles, respectively. FIGS. 2D and 2E show histograms of normalized current drop ($\Delta I/I_0$) and dwell time for p53TAD, respectively. FIGS. 2F and 2G show histograms of normalized current drop ($\Delta I/I_0$) and dwell time for GST-p53TAD, respectively. The histograms of FIGS. 2D to 2G were fitted to the single exponential decay function, and the mean values are indicated therein.

FIG. 3A shows 2D $^{15}$N-$^1$H HSQC spectra of free $^{15}$N-labeled MDM2 protein in 25 mM MES (pH 6.5) and 150 mM NaCl buffer. FIG. 3B shows a diagram illustrating 2D $^{15}$N-$^1$H HSQC spectra of $^{15}$N-labeled MDM2 bound with unlabeled GST-p53TAD (at a molar ratio of 1:1). FIG. 3C shows a diagram illustrating 2D $^{15}$N-$^1$H HSQC spectra of $^{15}$N-labeled MDM2 bound with unlabeled GST-p53TAD and treated with nutlin-3 (at a molar ratio of 1:1:1). FIG. 3D shows a diagram illustrating 2D $^{15}$N-$^1$H HSQC spectra of $^{15}$N-labeled MDM2 in the presence of unlabeled GST (at a molar ratio of 1:1). The proteins and nutlin-3 were mixed to a final concentration of 130 μM.

FIG. 4A shows 2D $^{15}$N-$^1$H HSQC spectra of free $^{15}$N-labeled MDM2 protein obtained in a buffer containing 1 M KCl, the same conditions as in the nanopore measurement. FIG. 4B shows a diagram illustrating 2D $^{15}$N-$^1$H HSQC spectra of $^{15}$N-labeled MDM2 (at a molar ratio of 1:1) bound with unlabeled GST-p53TAD (at a molar ratio of 1:1). FIG. 4C shows a diagram illustrating 2D $^{15}$N-$^1$H HSQC spectra of $^{15}$N-labeled MDM2 bound with unlabeled GST-p53TAD and treated with nutlin-3 (at a molar ratio of 1:1:1). The proteins and nutlin-3 were mixed to a final concentration of 100 μM, and the experiment was performed in a buffer containing 25 mM MES (pH 6.5), 150 mM NaCl, and 1 M KCl.

FIG. 5 shows diagrams illustrating the results of nanopore-based detection of the MDM2-p53TAD binding and the inhibition of the bound by nutlin-3. Nanopore-based analysis of free MDM2, MDM2-GST-p53TAD complex (at a molar ratio of 1:1), and the nutlin-3-treated complex (at a molar ratio of 1:1:1) was performed at the applied voltage of −175 mV. FIG. 5A shows diagrams illustrating current measured from the translocation of (1) free MDM2, (II) the MDM2-GST-p53TAD complex, (III) the complex treated with nutlin-3, and (IV) the complex treated with ABT-737. FIG. 5B shows a diagram illustrating the chemical structures of nutlin-3 and ABT-737. FIG. 5C shows a graph illustrating the scatter plots of the translocation of free MDM2 and nutlin-3-treated MDM2-GST-p53TAD complex through nanopores. Translocation events for free MDM2 and recovered MDM2 are indicated as blue and green squares, respectively. FIGS. 5D and 5E show histograms of normalized current drop ($\Delta I/I_0$) and dwell time for free MDM2 translocation, and FIGS. 5F and 5G are histograms of the recovered MDM2 translocation upon nutlin-3 treatment. The histograms of FIGS. 5D to 5G were each fitted to the lognormal function and the single exponential decay function, and the mean values are indicated in the histograms. FIG. 5H shows a schematic diagram of the nanopore-based detection of MDM2-GST-p53TAD complex formation and PPI inhibition by nutlin-3.

FIG. 6 shows diagrams illustrating the experimental result of the control group in comparison with the results shown in FIG. 5. FIG. 6A shows a diagram illustrating the result of a nanopore experiment in the presence of a buffer without any protein. FIG. 6B shows diagrams illustrating the result of nanopore experiment in the presence of nutlin-3 without any protein. FIG. 6C shows diagrams illustrating the result of a nanopore experiment in the presence of ABT-737 without protein. All nanopore experiments of FIG. 6 were measured at the negatively applied voltage of −175 mV in the presence of 1×PBS (pH 7.4) and 1 M KCl.

FIG. 7A shows a diagram illustrating molecular models of a free MLP fusion protein and an MLP fusion protein to which nutlin-3 is inhibited/bound. FIG. 7B shows a schematic diagram illustrating the translocation of MLP through nanopores (silicon nitride (SiN) nanopores with an effective thickness ($h_{eff}$) of 7 nm and a pore diameter ($d_p$) of 8 nm), in which the diagram on the left shows a single peak signal (type I) expected in a spherical structure and that on the right shows a double peak signal (type II) expected in a tMLP translocation through the alteration of MLP into a dumbbell-like structure by elongating a linker caused by inhibition of the p53TAD/MDM2 interaction by nutlin-3.

FIG. 8A shows a graph illustrating a typical I-V curve of a nanopore. FIG. 8B shows the results of the traces of continuous current of nanopore signals with respect to a free MLP and MLPs, where the molar ratio of nutlin-3 to the MLP is 1:1, 1:5, and 1:10. FIG. 8C shows a graph illustrating the percentages of type I and type II signals detected in each molar ratio of nutlin-3. FIGS. 8D to 8G show the results of continuous events of proteins, in which FIG. 8D represents the case of a free MLP, FIG. 8E represents a case when the molar ratio of nutlin-3 to the MLP is 1:1, FIG. 8F represents a case when the molar ratio is 1:5, and FIG. 8G represents a case when the MLP is 1:10. Among the single peaks of type I signals, a double peak with a fingerprint shape is indicated in the type II signals. The data was obtained at a 4.16 MHz sampling rate and low-pass filtered at 500 kHz.

FIGS. 9A to 9D show scatter plots of mean values of the normalized current blockade ($\Delta I/I_0$) and dwell time with respect to a free MLP and MLPs, where FIG. 9A represents the case of a free MLP, FIG. 9B represents a case when the molar ratio of nutlin-3 to the MLP is 1:1, FIG. 9C represents a case when the molar ratio is 1:5, and FIG. 9D represents a case when the MLP is 1:10. In scatter plots, type II events (star shape) are distinguished from type I events (square shape). FIGS. 9E to 9H show histograms illustrating the dwell time of type I and type II events with respect to a free MLP and MLPs, where FIG. 9E represents the case of a free MLP, FIG. 9F represents a case when the molar ratio of nutlin-3 to the MLP is 1:1, FIG. 9G represents a case when the molar ratio is 1:5, and FIG. 9H represents a case when the MLP is 1:10. The histograms with respect to the dwell time were fitted using the following Equation 1 so as to extract the diffusion coefficient ($D_p$) and free parameters of drift speed ($v_d$) within the pores.

$$F(t) = \frac{h_{eff}}{\sqrt{4\pi D_p t^3}} e^{-\frac{(h_{eff} - v_d t)^2}{4 D_p t}}$$ [Equation 1]

FIG. 10 shows the $^{15}$N-$^{1}$H HSQC spectra of MLPs according to the presence/absence of nutlin-3 in which cross peaks of a free MLP and MLPs bound to nutlin-3 are indicated. MLPs were treated with nutlin-3 to a molar ratio of 1:5. The circles and arrows represent the cross peaks recovered after the addition of nutlin-3.

FIG. 11 shows histograms illustrating the type II current drop between events, and all of the histograms were fitted to the Gaussian function.

BEST MODE

In order to achieve the above objects, an aspect of the present invention provides a method for screening a protein-protein interaction inhibitor using a nanopore, comprising (a) forming a protein complex in which a first protein and a second protein are bound by a protein-protein interaction; (b) measuring an electrical signal generated while the protein complex passes through the nanopore; and (c) treating the protein complex with a protein-protein interaction inhibitor candidate, and measuring an electrical signal generated while the protein complex passes through the nanopore.

The method for screening protein-protein interaction inhibitors enables discovery of protein-protein interaction inhibitors by measuring and comparing electrical signals of a protein that varies depending on the binding-inhibiting activity of the inhibitor candidates and protein complexes thereof.

The varying electrical signal includes both cases when the intensity or frequency of electrical signal increases and decreases. For example, when the electrophoretic force increases, which facilitates translocation through the nanopores due to the charge property that is subject to change by the inhibition of complex formation, the intensity or frequency of the signal may increase, whereas when the electrophoretic force decreases, the signal strength or frequency may decrease.

As used herein, the terms "first protein" and "second protein" refer to proteins capable of forming a complex through their interactions, and it is preferable that one of these proteins be positively charged while the other is negatively charged, but the first protein and second protein are not limited thereto.

Specifically, the first protein may be mouse double minute 2 (MDM2) and the second protein may be p53, or the first protein may be p53 and the second protein may be MDM2. More specifically, the first protein and second protein may be the N-terminal domain of MDM2 (residues 3 to 109), or may be residues 1 to 73 of p53 transactivation domain (TAD), but the first protein and second protein are not limited thereto. The inhibition of the complex of MDM2 and p53 can recover the functions of p53 and induce cancer cell death, and thus is an important target for chemotherapy.

In an exemplary embodiment, a complex inhibitor which targets the complex of MDM2 and p53TAD was screened using nanopores.

With respect to the term "protein complex", any protein complex in which two or more electrically charged proteins are bound is included in the scope of the present invention without limitation in terms of the method, location, size, etc. of the binding.

Specifically, the formed protein complex may have an increased or decreased intensity or frequency of the electrical signal generated when passing through the nanopores compared to that of the first protein or second protein before the formation of the complex. The formation of the protein complex changes the current that passes through the nanopore by changing the charge property of the proteins before and after the formation of a protein complex. Accordingly, the formation and inhibition of a protein complex can be confirmed by the changes in the intensity or frequency of the electrical signal.

Further, the protein complex of the present invention may be a protein complex formed by an interaction between two or more proteins, and each of the proteins that form a protein complex may be in a state independent from each other or may be linked by a linker.

In a protein complex formed by an interaction of proteins that are not linked by a linker but are in states independent from each other, the electrical signal (e.g., intensity, frequency, etc.) may increase or decrease according to the presence/absence of an interaction between the proteins, whereas a protein complex formed by an interaction of proteins that are linked by a linker may show a different pattern in electrical signals according to the presence/absence of an interaction.

As used herein, the term "linker" may refer to a peptide linker consisting of at least one amino acid, but the linker is not limited thereto. Specifically, the peptide linker may include at least one amino acid (e.g., 1 to 1,000 amino acids), but the peptide linker is not particularly limited with regard to the number or type of the amino acids. Any peptide linker known in the art (e.g., a $[GS]_x$ linker, $[GGGS]_x$ linker, $[GGGGS]_x$ linker, etc.), in which x is a natural number of 1 or greater (e.g., 1, 2, 3, 4, 5, or greater), and more specifically, the amino acid sequence of "GGGS", but the peptide linker is not limited thereto. Additionally, the linker may be $(GGGS)_4$, $(GS)_8$, or $(GGGS)_3$, but the linker is not limited thereto.

Specifically, the protein complex in which the first protein and the second protein are linked by a linker may change the pattern of the electrical signals that pass through the nanopores, compared to when the complex is formed. In an exemplary embodiment, when the measured electrical pattern shows multiple peaks, the inhibition of protein-protein interaction may be confirmed, but the confirmation of the inhibition of protein-protein interaction is not. limited thereto.

In an exemplary embodiment of the present invention, it was confirmed that the protein complex of MDM2 and p53TAD generated a single-peak electrical signal, whereas the protein complex treated with nutlin-3 (i.e., an interaction inhibitor) generated a double-peak electrical signal, and from these results, it was confirmed that protein-protein interaction inhibitors can be screened based on the pattern (shape) of electrical signals.

The protein complex of the present invention mediates many different physiological activities that may occur due to protein-protein interactions, and in particular, may be involved in the onset and progress of various diseases including cancers, degenerative diseases (dementia, etc.), metabolic diseases (diabetes, obesity, hyperlipidemia, etc.), cranial nerve diseases (Alzheimer's disease, Parkinson's disease, stroke, etc.), cardiovascular diseases (myocardial infarction, stroke, atherosclerosis, etc.), microbial infectious diseases (flu, hepatitis, etc.), and immune diseases (rheumatoid arthritis, etc.). The screening method of the present invention, by screening an inhibitor which inhibits interactions in the complex, enables discovery of therapeutic drugs, in addition to anti-cancer drugs, for degenerative diseases (dementia, etc.), metabolic diseases (diabetes, obesity, hyperlipidemia, etc.), cardiovascular diseases (myocardial infarction, stroke, atherosclerosis, etc.), microbial infectious diseases (flu, hepatitis, etc.), and immune diseases (rheumatoid arthritis, etc.)).

In other words, the protein-protein interaction inhibitors may be therapeutic agents for cancers or one or more diseases of the following (I) to (V):

(I) the degenerative disease is dementia;

(II) the metabolic disease is diabetes, obesity, or hyperlipidemia;

(II) the cardiovascular disease is myocardial infarction, stroke, or atherosclerosis;

(IV) the microbial infectious disease is flu or hepatitis; or (V) the immune disease is rheumatoid arthritis.

Specifically, the screening method of the present invention may further comprise (a') measuring the intensity or frequency of an electrical signal generated while the first or second protein passes through the nanopores, before (a); more specifically, may comprise comparing the intensity or frequency of the electrical signal measured in (a') and that measured in (c).

According to the screening method of the present invention, an inhibitor can be screened by comparing the intensity or frequency of an electrical signal generated while the first or second protein passes through the nanopores and that of an electrical signal generated by the protein complex treated with an inhibitor candidate and determining whether the signal recovers its original intensity or frequency before the formation of the protein complex due to the treatment with the inhibitor candidate.

In an exemplary embodiment, the intensity or frequency of signal generated while each of the MDM2 and p53TAD proteins passing through nanopores before the formation of a complex thereof decreases when the complex is formed, but recovers its original intensity after the treatment with nutlin-3.

Further, to increase the measurement sensitivity of nanopores, the protein complex of the present invention may further comprise a third protein, in addition to the first and second proteins that form a protein complex, which can be bound to a linker without significantly changing the net charge of the first or second protein. More specifically, the third protein may be selected from the group of typical globular proteins consisting of glutathione S-transferase (GST), maltose binding protein (MBP), thioredoxin (TRX), green fluorescent protein (GFP), and chitin binding protein (CBD), but the third protein is not limited thereto. The type and binding method of the linker may be a peptide linkage or non-peptide linkage such as polyethylene glycol, but is not limited thereto, and any chemical binding method is feasible.

In an exemplary embodiment, the protein binding and the inhibition thereof were examined using GST-p53TAD fused with GST, which has a smaller diameter than the nanopore and thus has a large-sized protein and does not significantly change the net charge of p53TAD. As a result, it was confirmed that GST-p53TAD has an improved signal-to-noise ratio while exhibiting similar electrical characteristics to p53TAD.

As used herein, the term "nanopore", in which voltage is applied at both ends, can drive a protein or protein complex from a first section to a second section. The protein or protein complex that has passed through the nanopore may generate different electrical signals according to its charge property.

Specifically, it is preferable that the diameter of the nanopores be 5 nm to 20 nm, but the diameter is not limited thereto.

In an exemplary embodiment, LPCVD $SiN_x$ membrane was fabricated on an insulating Pyrex substrate and TEM was used to prepare a nanopore. The nanopore has a diameter of about 10 nm to 15 nm, and the formation and dissociation of the protein complex were detected using the same.

As used herein, the term "electrical signal" refers to all types of signals generated while a protein or a protein complex passes through a nanopore. The protein or protein complex that passes through the nanopore of the present invention can generate electrical signals different from each other according to the presence/absence of a protein-protein interaction, protein structures, etc. Specifically, the protein or protein complex, which is positively or negatively charged, may generate an electrical signal while passing through a voltage-applied nanopore by electrophoretic force. An example of the electrical signal may be a current, but the signal is not limited thereto. Whether the protein or protein complex has passed through the nanopore and the amount thereof can be measured by the electrical signal. For the purpose of the present invention, the type of the signal is not limited as long as it allows determination of whether the protein is bound based on the generated electrical signal; however, a current drop or dwell time is preferred. In the present invention, protein-protein interactions can be analyzed in various aspects by measuring the intensity, frequency, pattern, etc. of the electrical signals.

With respect to the term "protein-protein interaction inhibitor", any protein-protein interaction inhibitors capable of recovering a protein to its original form before binding by inhibiting the binding of the protein complex formed by a protein-protein interaction are included in the present invention without limitation. The inhibitors inhibit the protein binding through competitive inhibition and recover each protein to its original form before binding, thereby recovering its electrical signal to that before binding. By measuring the intensity of the electrical signal, the action of the inhibitor can be confirmed.

Specifically, the protein-protein interaction inhibitor may be a therapeutic agent selected from the group consisting of cancers, degenerative diseases, metabolic diseases, cardiovascular diseases, microbial infectious diseases, and immune diseases; in particular, an anticancer drug. The anticancer drug can have prophylactic and therapeutic effects on cancers by inhibiting the binding of a protein targeted for chemotherapy.

As used herein, the term "candidate" refers to any substance expected to have an effect of inhibiting the protein binding; for example, any molecule such as proteins, oligopeptides, small organic molecules, polysaccharides, polynucleotides, various compounds, etc., but is not limited thereto. Such candidate includes not only a natural substance but also a synthetic substance. Any substance expected to be capable of exhibiting the effect of inhibiting the protein complex can be used as the candidate without limitation.

The screening method of the present invention may determine the candidate as a protein-protein interaction inhibitor if the candidate inhibits the protein binding.

In an exemplary embodiment, the inhibitory effect of nutlin-3 on protein binding was confirmed by the screening method of the present invention using nutlin-3 as an MDM2-p53TAD interaction inhibitor candidate. It was confirmed that the signal generated while each of the MDM2 and p53TAD proteins passed through the nanopore decreased in intensity due to the formation of a complex and its original intensity was recovered after nutlin-3 treatment, thereby verifying the effectiveness of the screening method of the present invention.

It was confirmed in another exemplary embodiment that the formation of a protein complex was not inhibited by ABT-737, and thus, there was no change in the signal generated during translocation through a nanopore. From this result, it was confirmed that the screening method of the present invention can effectively discover protein binding inhibitors.

The inhibitory effect of nutlin-3 against the protein binding discovered by the screening method of the present invention was further confirmed through NMR experiments in another exemplary embodiment. As a result, nutlin-3 was confirmed to actually inhibit the binding of MDM2 and p53TAD, which indicates that the nutlin-3 used in the screening method of the present invention actually plays a role as a protein binding inhibitor.

As used herein, the term "screening" refers to detecting of a substance having a particular property such as having sensitivity or activity to a particular chemical substance. The screening method of the present invention aims to discover an inhibitor which inhibits protein binding by screening the inhibitors.

The screening method of the present invention enables discovery of a protein-protein interaction inhibitor by comparing the electrical signals measured before and after the treatment with an inhibitor to find whether the binding formation is inhibited. Inhibitors that can be discovered by the screening method of the present invention are included in the present invention without limitation as long as they can induce different electrical signals according to the translocation through the nanopores.

Another aspect of the present invention provides a method for analyzing the structure of an interacting protein using a nanopore, comprising measuring the electrical signal generated while a protein or protein complex passes through the nanopore.

As used herein, the terms "nanopore", "electrical signal", "first protein", "second protein", "protein complex", and "linker" are the same as explained above. Specifically, for the analysis of the structure of a protein that is not linked by a linker, in the method for analyzing the protein structure of the present invention, the electrical signal to be measured is the time required for a free protein to pass through a nanopore and the intensity of the electrical signal, and the method further comprises: plotting the measured nanopore translocation time and the intensity of the electrical signal in a scatter plot, in which the free protein is determined as having a typical structure when the data shown in the scatter plot is distributed to be heavily concentrated in a local area, thus enabling the calculation of the maximum frequency value of the Gaussian distribution; and the free protein is determined as having an atypical structure when the data is distributed in a linear distribution. In particular, the Gaussian distribution, known as the standard distribution, refers to a distribution expressed as $N(x|\mu,\sigma^2)=1/(2\pi\sigma^2)^{1/2}\exp\{-\frac{1}{2}\sigma^2(x-\mu)^2\}$ ($\mu$: mean; $\sigma^2$: standard deviation). The maximum frequency value of the Gaussian distribution may be calculated by the central limit theorem, but the calculation is not limited thereto. Additionally, the linear distribution may mean those which can be expressed in the form of $f(x)=ax$.

Additionally, for the analysis of the structure between two proteins linked by a linker, the method for analyzing the protein structure of the present invention may further comprise a step in which the protein complex is determined as having a typical structure comprising a spherical shape when the pattern of the measured electrical signal is a single peak, and the protein complex is determined as having an atypical structure including a dumbbell shape and a linear shape when the measured electrical signal has a double peak.

In an exemplary embodiment of the present invention, it was confirmed that the MDM2-GST-p53TAD complex, after nutlin-3 treatment, recovered the time required for the translocation of nanopores and the frequency or intensity of the signals generated as the complex passed through the nanopores to the level of electrical signals generated when the MDM2 passed through the nanopores in a free state. Based on these results, the changes in protein structures can be analyzed by comparing the electrical signal generated when a protein complex passed through nanopores with that generated when a free protein passed through nanopores, followed by determining that the protein has an atypical structure similar to that of a free protein when the electrical signal is reduced, and determining that the protein has a typical structure when the electrical signal is increased.

Additionally, in an exemplary embodiment of the present invention, it was confirmed that the electrical signal with a single peak generated when the MDM2-p53TAD complex, which is bound by a $(GGGS)_4$ linker, passes through nanopores is converted into an electrical signal with a double peak after nutlin-3 treatment of the MDM2-p53TAD complex. This is because the structure of the protein complex varies depending on the presence/absence of an interaction between the two proteins linked at both ends of the linker. Based on this result, the present inventors have discovered that the changes in structures of protein complexes which are formed as a result of a protein-protein interaction can be analyzed using the nanopores of the present invention. That is, in the present invention, electrical signals generated while passing through nanopores vary depending on the protein structures, and thus, the changes in protein structures can be analyzed by comparing the electrical signals before and after the protein-protein interaction.

Still another aspect of the present invention provides a method for analyzing a protein-protein interaction using a nanopore, comprising (a) passing a first protein or second protein through a nanopore; and measuring the electrical signal generated therefrom; (b) forming a protein complex in which the first protein and the second protein are bound by a protein-protein interaction; and measuring the electrical signal generated while the protein complex passes through the nanopore; and (c) comparing the electrical signals generated in (a) and (b).

As used herein, the terms "nanopore", "electrical signal", "first protein", and "second protein" are the same as explained above.

Specifically, for the analysis of a protein-protein interaction between two proteins which are not linked by a linker but in a state independent of each other, the method for analyzing the protein-protein interaction of the present invention may further comprise (d) determining that a protein-protein interaction is formed between a first protein and a second protein when the frequency of the electrical signal measured in (b) is reduced compared to the frequency of the electrical signal measured in (a).

Additionally, for the analysis of the structure between two proteins linked by a linker, the method for analyzing the protein-protein interaction of the present invention may be to link the second protein to the first protein as explained above, and specifically, the method may further comprise (d) determining that a protein-protein interaction is formed between the first protein and the second protein when the electrical signal generated during the translocation of nanopores by the first protein and the second protein linked by a linker shows a single peak; and determining that a protein-protein interaction is not formed between the first protein and the second protein when the electrical signal generated during the translocation of nanopores by the first protein and the second protein linked by a linker shows multiple peaks.

The method for analyzing the protein-protein interaction of the present invention may be performed by the analysis of various aspects of the protein-protein interaction (i.e., presence/absence of an interaction, binding affinity between proteins, structures of protein complexes, etc.) through electrical signals generated when proteins or protein complexes pass through nanopores.

In an exemplary embodiment of the present invention, it was confirmed that when the MDM2-GST-p53TAD complex was treated with an interaction inhibitor (i.e., nutlin-3), the electrical signal generated while the MDM2-GST-p53TAD complex passes through nanopores was recovered to the electrical signal generated while a free MDM2 passes through nanopores. Based on this result, the protein-protein interaction can be analyzed by comparing the electrical signal generated while the first protein and the second protein were allowed to contact and pass through nanopores with the electrical signal generated while the first or second protein passes through nanopores in a free state; and determining that a protein-protein interaction is formed between the first protein and the second protein when the electrical signal is reduced.

Additionally, in an exemplary embodiment of the present invention, it was confirmed that the electrical signal with a single peak generated when the MDM2-GST-p53TAD complex bound by a $(GGGS)_4$ linker passes through nanopores is converted to an electrical signal with a double peak after the treatment of the MDM2-GST-p53TAD with nutlin-3. This is because the structure of the protein complex varies depending on the presence/absence of an interaction between the two proteins linked at both ends of the linker. Based on this result, the present invention can analyze a protein-protein interaction based on the presence/absence of a protein-protein interaction by determining that a protein-protein interaction is formed when the electric signal generated shows a single peak, whereas a protein-protein interaction is not formed when the electric signal generated shows a double peak.

Still another aspect of the present invention provides a kit or equipment for performing the method of the present invention described above. Specifically, the present invention provides a kit or equipment comprising nanopores capable of applying a voltage and a constitution enabling the measurement of an electrical signal.

As used herein, the term "kit" may further comprise an instruction manual describing optimal conditions for performing reactions. The instruction manual comprises instructions on the surface of the package including a pamphlet or leaflet-type brochure, a kit, and labels attached to the kit. In addition, the brochure may include information published or provided through an electronic medium such as the internet.

Protein binding inhibitors can be discovered from candidate substances of protein-protein interaction inhibitors using a kit for screening protein-protein interaction inhibitors. Additionally, the kit for verifying the efficacy of protein-protein interaction inhibitors of the present invention may be one which, after treating a protein complex with a substance determined as a protein-protein interaction inhibitor, determines that the substance is a more effective protein binding inhibitor as the substance has a greater inhibitory effect against protein binding. Additionally, the kit for verifying the anticancer efficacy of the present invention may be one which, after treating a protein complex to be a target for cancer treatment with a substance determined as an anticancer agent, determines that the substance is a more effective anticancer agent as the substance has a greater inhibitory effect against protein binding. Further, the kit of the present invention may be one which has the use of analyzing the structures of protein complexes or the use of analyzing the protein-protein interactions, and other constitutions suitable for the above uses may further be added.

The "equipment" of the present invention may be that which has the use of screening protein-protein interaction inhibitors, use of analyzing the structures of protein complexes, or use of analyzing protein-protein interactions, and the equipment may further comprise an instruction manual describing optimal conditions for performing reactions. The instruction manual comprises instructions on the surface of the package including a pamphlet or leaflet-type brochure, a kit, and labels attached to the kit. In addition, the brochure may include information published or provided through an electronic medium such as the internet.

The equipment for screening protein-protein interaction inhibitors of the present invention comprises nanopores capable of applying a voltage at both ends thereof. The equipment can discover protein-protein interaction inhibitors by measuring and comparing the electrical signals of protein complexes or protein complexes treated with a binding inhibitor candidate that pass through the nanopores, and determining the presence/absence of any change in the intensity of the signals. Additionally, the equipment for verifying the efficacy of the protein-protein interaction inhibitors of the present invention may be that which comprises nanopores capable of applying a voltage at both ends thereof, and measures the electrical signal of a protein complex treated with a substance determined as an inhibitor and determines that the substance is an effective inhibitor against protein binding. The equipment of the present invention may be that which further comprises a constitution suitable for the use of screening protein-protein interaction inhibitors, use of analyzing the structures of protein complexes, or use of analyzing protein-protein interactions.

MODE FOR INVENTION

Hereinafter, the present invention will be described in more detail with reference to the following exemplary embodiments. However, these Examples are for illustrative purposes only, and the invention is not intended to be limited by these Examples.

Example 1: Expression and Purification of Protein

In order to verify the method for screening protein-protein interaction inhibitors using a nanopore, the present inventors have selected MDM2 and p53TAD, representative interacting proteins, and used their binding domains. Additionally, to confirm the method for analyzing the presence/absence of a protein-protein interaction between proteins linked by a linker using the nanopores of the present invention and confirm the changes in the structures thereof, the present inventors have selected MDM2 and p53TAD as representative interacting proteins, and linked these proteins using a (GGGS)$_4$ a linker. Additionally, nutlin-3, which is widely known to inhibit interactions between MDM2 and p53TAD, and ABT-737 as a reference group were representatively used in the experiments.

Specifically, the N-terminal domain of the recombinant MDM2 (residues 3 to 109, PDB code: 1YCR) used in the experiment was expressed in *E. coli* BL21 (DE3) by induction with 0.4 mM isopropyl-β-D-thiogalactoside (IPTG) at an OD600 of 0.9 overnight at 20° C. The protein was precipitated with ammonium sulfate and purified using HiTrap™ SP and QSepharose ion-exchange columns (GE Healthcare) and a gel-filtration column (HiLoad 16/60 Superdex G75, Pharmacia). For the NMR experiments, $^{15}$N-labeled MDM2 was expressed in minimal media containing $^{15}$N—NH$_4$Cl and purified as described above.

The N-terminal GST-fused p53TAD (residues 1 to 73) was expressed in *E. coli* BL 21 (DE3) by inducing with 0.3 mM IPTG. GST-p53TAD was purified by GST affinity chromatography. The GST tag bound to p53TAD was decomposed with thrombin and then removed by GST affinity chromatography. Further, p53TAD was purified by anion-exchange chromatography (SOURCE 15Q, GE Healthcare) and translocate over a gel-filtration column (HiLoad™ 16/60 Superdex™ G75, Pharmacia).

A DNA construct encoding an MLP-fused protein [MDM2 (residues 3 to 109)-linker-p53TAD (residues 1 to 73)-GST] was cloned into the pET-21a vector. The MLP construct comprises a (GGGS)$_4$ linker consisting of 16 amino acid residues between the C-terminus of MDM2 and the N-terminus of p53TAD. The MLP protein was overexpressed in *E. coli* Rosetta™ 2 by inducing at an OD600 of 0.7 with 0.5 mM isopropyl-β-D-thiogalactoside (IPTG). After the induction with IPTG, the cells were grown in LB or M9 minimal medium at 20° C. for 12 hours. The MLP protein was purified by GST affinity chromatography (GSTrap™, GE Healthcare), anion exchange chromatography (Hitrap™ Q, GE Healthcare), and gel-filtration chromatography (HiLoad® 16/600 Superdex® 75 μg, GE Healthcare). For the NMR experiments, $^{15}$N-labeled MLP protein was expressed in M9 minimal medium containing $^{15}$N—NH$_4$Cl and purified as described above.

The inhibitors nutlin-3 (581.5 g/mol, Cayman Chemical Inc.) and ABT-737 (813.43 g/mol, Selleckchem) were purchased.

MDM2 and GST-p53TAD proteins were bound by incubating in 1×PBS buffer (pH 7.4) at room temperature for 2 hours and diluted to a final concentration of 100 nM with a buffer containing 1 M KCl for the nanopore experiment. Nutlin-3 or ABT-737 was bound to the proteins in 1×PBS (pH 7.4) and then diluted with 1×PBS containing 1 M KCl for the nanopore experiments.

Example 2: Nanopore Experiments

After depositing low-stress 100 nm LPCVD SiN$_x$ on a 500 μm Si substrate, photolithography and reactive ion etching were performed thereon. After performing KOH wet etching, the SiN$_x$ membrane (2×2 mm$^2$ window) was transferred to a Pyrex substrate manufactured as previously described. The membrane was etched with CF$_4$ plasma to a 20 nm thickness (etch rate of about 15 nm/min).

The nanopore was drilled using TEM employing a highly focused electron beam. The nanopore was treated with air plasma on both sides for 3 minutes prior to use and then assembled in a customized acrylic flow cell and tightly sealed with polydimethylsiloxane (PDMS).

1×PBS buffer (pH 7.4) containing 1 M KCl electrolytes was introduced into the flow cell to hydrate the nanopore. The nanopore cell was connected to a Ag/AgCl electrode and a patch clamp system in a Faraday cage.

In all of the experiments, proteins and inhibitors were injected at a concentration of 100 nM into the cis-side of the flow cell. Additionally, the concentration of MDM2-linker-p53TAD (MLP) was fixed at 100 nM and injected into a cis chamber. The translocation experiment was performed at a potential of 200 mV crossing over the membrane using the Ag/AgCl electrode. The ionic current was measured using an Axopatch 200B patch clamp amplifier (Molecular Devices, USA) at a sampling rate of 250 kHz and filtered using electronic low-pass Bessel filtration (10 kHz).

Data were collected at pores with a diameter of about 10 nm to 15 nm and analyzed using the pClamp 10.4 software. The exact diameter of the nanopores was determined by measuring the I-V characteristics.

The translocation events of the proteins were identified using current thresholds greater than the noise level with baseline correction. The mean values of the normalized current blockade ($\Delta I/I_0$) and the dwell time were calculated based on the peak values in the histograms calibrated to a single exponential decay function.

Example 3: NMR Experiments

All of the NMR experiments were performed at 298 K using a Bruker 900 MHz spectrometer equipped with a cryogenic probe at the Korea Basic Science Institute (KBSI: Ochang, Korea). 2D $^1$H-$^{15}$N HSQC spectra of $^{15}$N-labeled MDM2 were obtained in an environment with or without unlabeled GSTp53TAD, unlabeled GST tag, or a mixture of unlabeled GST-p53TAD and nutlin-3. Additionally, the 2D $^{15}$N-$^1$H HSQC spectra of MLP were obtained at 298 K in an environment with or without a nutlin-3 mixture.

The proteins and inhibitor were combined at equal molar ratios to a final concentration of 130 μM. The NMR buffer contained 25 mM MES (pH 6.5) and 150 mM NaCl or 25 mM MES (pH 6.5), 150 mM NaCl, and 1 M KCl. Additionally, nutlin-3 was treated to prepare the 100 μM MLP protein at a 1:5 molar ratio. The NMR data was processed using the TopSpin 3.1 (Bruker) and NMRPipe2 software.

The results of the experiments were analyzed as shown in the Experimental Examples below.

Experimental Example 1: Verification of Translocation of MDM2 and GST-p53TAD Using Nanopores Experimental Example 1-1: Passing of MDM2 Through Nanopores The present inventors have attempted to detect the MDM2-p53TAD interactions and the inhibition of MDM2-p53TAD interactions by inhibitors using solid-state nanopores.

First, nanopores sized about 10 nm to 15 nm were manufactured using a low-pressure chemical vapor deposition (LPCVD) SiN$_x$ membrane which was transferred to a Pyrex substrate.

Meanwhile, the structure of the N-terminal p53TAD-binding domain of MDM2 (PDB code: 1YCR) had a size of 3.1 nm×3.5 nm×4.2 nm, with a theoretical volume of 45.57 nm$^3$ (FIG. 1A).

At the applied voltage of −175 mV across the nanopore, the positively charged MDM2 domain (residues 3 to 19, net positive charge at pH 7.4=+2.9 e, pI=9.02) was electrophoretically translocated from one chamber toward the negative electrode in the other chamber (FIG. 1B). The translocation of MDM2 through the nanopore caused a temporary reduction in the ionic current, thereby enabling the detection of MDM2 translocation events at the single-molecule level through nanopores (FIG. 1C).

The ionic current was measured using an Axopatch 200B amplifier (Molecular Devices, USA) at a sampling rate of 250 kHz and filtered with a 10 kHz low-pass Bessel filter. Current traces with regard to 100 nM MDM2 measured in comparison with the control group, which comprises only a buffer, at an optimized electrolyte concentration of 1 M KCl are shown (FIG. 1C). The translocation events of proteins were determined by the dwell time and the normalized blockade of the open pore current ($\Delta I/I_0$; $\Delta I$=magnitude of current drop, $I_0$=open pore current). A scatter plot of the $\Delta I/I_0$ vs. dwell time of a total of 1,372 MDM2 translocation events is shown in FIG. 1E.

For the MDM2 translocation events, fitting the $\Delta I/I_0$ and dwell time histograms to the single exponential decay function (FIGS. 1F and 1G) revealed mean ($\Delta I/I_0$) and dwell time values of 0.016 ms and 0.05 ms, respectively.

To date, nanopore measurement is limited to relatively small proteins due to the poor signal-to-noise ratio. However, in the present invention, the application of a Pyrex substrate to the nanopore membrane significantly improved the signal-to-noise ratio of the detected ionic current blockade.

As a result of the nanopore experiment for MDM2 translocation, the ionic current root mean square (RMS) noise level (IRMs) was measured to be 7 pA to 10 pA. That is, the signal-to-noise ratio of the present invention was high enough to detect the translocation of MDM through nanopores despite the small size of the N-terminal domain of MDM2.

Experimental Example 1-2: Passing of GST-p53TAD Through Nanopores

The present inventors have attempted to detect the translocation of negatively charged 100 nM p53TAD (−14.2 e at pH 7.4, pI=3.6) at the applied voltage of +100 mV (FIG. 2A).

To further improve the signal-to-noise ratio of the current blockade caused by the translocation of p53TAD (residues 1 to 73, MW=8.2 kDa), the present inventors have introduced a glutathione S-transferase (GST) tag at the N-terminus of p53TAD. This is because the GST tag is a relatively large protein (26.3 kDa) with a net charge of −2.9 e at pH 7.4 and the increase of the molecular size of a protein without significantly changing its net charge can enhance the signal-to-noise ratio of the current blockade signal caused by protein translocation. As expected, the translocation of GST-p53TAD (−16.9 e at pH 7.4) showed a dramatic increase in the sensitivity of the current blockade signal (FIGS. 2A and 2B).

Therefore, the present inventors have used GST-p53TAD for subsequent nanopore experiments to detect the interaction between p53TAD and MDM2 and the inhibition of the interaction by small molecules.

Experimental Example 1-3: Comparison of p53TAD and GST-p53TAD

The scatter plots shown in FIG. 2C revealed a remarkably difference in distribution between p53TAD and GST-p53TAD. While GST-p53TAD translocation events are concentrated in the dwell time of 0.1 ms, the translocation events for intact p53TAD showed widely dispersed dwell time ranging from 0.05 ms to 10 ms. In the histograms of dwell time and $\Delta I/I_0$, the p53TAD translocation events displayed a lower mean value ($\Delta I/I_0$) of 0.012 and an increased mean dwell time of 0.13 ms, compared to those of GST-p53TAD whose $\Delta I/I_0$ and dwell time values were 0.037 ms and 0.07 ms, respectively (FIGS. 2D to 2G).

The distinct difference in translocation between p53TAD and GST-p53TAD may be due to the difference in their structures. p53TAD is known to be an intrinsically disordered protein (IDP) that is mostly unfolded but is able to form a transient secondary structure in some regions. On the other hand, GST-p53TAD is mostly known to be a globular protein due to the character of the GST tag that is readily folded. The unfolded, linear conformation of p53TAD significantly increases the dwell time of translocation, and its unique distribution spanning over a wide range of 0.05 ms to 10 ms reflects the conformational heterogeneity of the protein (FIG. 2C).

Taken together, the nanopore analysis of the p53TAD translocation confirmed that structural differences between the unfolded and folded proteins can be detected by solid-state nanopores at a single-molecule level.

Experimental Example 2: Verification of Inhibition of Nutlin-3 Against MDM2-GST-p53TAD Binding Using Nanopore The present inventors have monitored the interaction between MDM2 and GST-p53TAD and its inhibition by nutlin-3 using a Pyrex-based solid-state nanopore manufactured in the above Examples.

FIG. 5 shows the observation results of nanopore measurements of a complex of free MDM2 and the MDM2-GSTp53TAD in a system containing about 10 nm-sized nanopores at the applied voltage of −175 mV. In comparison with the translocation of a large number of free MDM2, the number of translocation events for the MDM2-GST-p53TAD complex through the nanopores was rapidly reduced to a negligible level (FIG. 5A). During the formation of the complex, the net charge of the proteins at pH 7.4 changed from +2.9 e to −13.7 e due to charge masking of MDM2 by the negatively charged GSTp53TAD. As a result, it was confirmed that the overall negatively charged protein complex could not translocate through the nanopores at the applied negative voltage.

Based on the above results, the present inventors have attempted to monitor the binding and dissociation of MDM2 and GST-p53TAD using solid-state nanopores at the nanomolar scale.

In this regard, the present inventors have attempted to monitor the nanopore translocation of the MDM2-GST-p53TAD complex in the presence of nutlin-3. After the treatment of the complex with nutlin-3, the translocation of MDM2 was mostly recovered (FIG. 5A).

This indicates that the binding of the MDM2-GST-p53TAD is inhibited by nutlin-3, and MDM2 is dissociated from the complex. The experimental data of the free and nutlin-3-recovered MDM2 translocations through the nanopores was analyzed and compared in FIGS. 5C to 5G.

From the scatter plot of current drop vs. dwell time for all translocation events, the free and recovered MDM2 translocations were identified to exhibit the same distribution for the translocation through nanopores. In addition, from the histograms of current drop and dwell time, both the free and recovered MDM2 translocation events were confirmed to have similar mean values ($\Delta I/I_0$) and dwell time; e.g., the free MDM2 ($\Delta I/I_0$: 0.011 and dwell time: 0.06 ms) and the recovered MDM2 ($\Delta I/I_0$: 0.012 and dwell time: 0.06 ms).

Further, to confirm whether the MDM2-GST-p53TAD binding is specifically inhibited by nutlin-3, the nanopore experiment was repeated using ABT-737, which is an inhibitor of Bcl-2 family proteins that does not bind to MDM2, as a negative control.

Consequently, unlike nutlin-3, ABT-737 was unable to recover the translocation of MDM2 (FIG. 5A), and this confirmed that nutlin-3 specifically blocks the interaction between MDM2 and GST-p53TAD.

Additionally, the present inventors have measured the nanopores in the protein-free buffer control, 100 nM free nutlin-3, and 100 nM free ABT-737, and found that there was no signal that passed through the nanopores, confirming that the translocation of the recovered MDM2 in FIG. 5A is a result of the protein interaction inhibition by nutlin-3 (FIG. 6).

Experimental Example 3: Verification of the Inhibition of MDM2-GST-p53TAD) Binding by Nutlin-3 Using NMR The present inventors have conducted NMR experiments to examine the interaction between MDM2 and GST-p53TAD and the inhibition of the interaction by small molecules so as to confirm the effect of the method of the present invention for screening the protein-protein interaction inhibitors using nanopores.

Specifically, to monitor the binding and dissociation between MDM2 and GST-p53TAD, the present inventors have recorded 2D $^{15}$N-$^1$H heteronuclear single quantum correlation (HSQC) spectra of $^{15}$N-labeled MDM2 in an environment with or without GST-p53TAD (FIGS. 3A and 3B). When $^{15}$N-labeled MDM2 was bound to GST-p53TAD, most of the $^{15}$N-$^1$H cross-peaks in MDM2 disappeared due to the severe line broadening, indicating the formation of a complex between MDM2 and GST-p53TAD. The GST-p53TAD binding was confirmed to increase the tumbling time and decrease the $T_2$ relaxation time of the protein complex (FIG. 3B). Such a change was not observed when only GST was added (FIG. 3D), which suggests that GST alone cannot bind to MDM2. As nutlin-3, a potent MDM2 inhibitor, can bind to MDM2 with higher affinity than p53TAD does, it can interfere with the interaction between MDM2 and p53TAD ($K_d$=0.6 μM).

Actually, the addition of nutlin-3 to the protein binding restored all of the missing cross-peaks of the $^{15}$N-labeled MDM2 (FIG. 3C), thus confirming that the binding of nutlin-3 induces the release of MDM2 from the GST-p53TAD-bound complex.

In addition, the present inventors have confirmed based on FIG. 3C that the chemical shift perturbations in MDM2 induced by nutlin-3 results in formation of a complex between MDM2 and nutlin-3.

The present inventors have repeated and compared NMR experiments in the presence of 1 M KCl using the same experimental conditions as the nanopore experiment in FIG. 5. The results showed that the interaction between MDM2 and GST-p53TAD and the inhibition of the interaction by nutlin-3 were also observed at a high concentration of 1 M KCl as in the NMR results of FIG. 3 (FIG. 4).

In light of all of the above NMR experiment results, the present inventors have confirmed the interaction between MDM2 and GST-p53TAD and competitive inhibition thereof caused by nutlin-3.

Experimental Example 4: Detection of Interactions Between Proteins of MDM2-Linker-p53TAD (MLP) Through Nanopores in the Presence/Absence of Nutlin-3

To improve the signal-to-noise ratio and temporal resolution of a detection system, the present inventors have designed a fusion protein complex, MDM2-linker-p53TAD (MLP), where p53TAD comprising a GST tag at the C-terminus of p53 and MDM2 are linked by 16 amino acids, for the effective detection of structural changes due to a protein-protein interaction, using $SiN_x$ nanopores having a substrate with strong insulation bound to a high frequency amplifier (4.16 MHz).

FIG. 7 shows the observation results of morphological changes in a free MLP and changes in electrical signals according to the addition of nutlin-3 in a system comprising nanopores having a thickness of about 8 nm at the applied voltage of 200 mV. As can be confirmed in FIG. 7A, the MLP shows a closed shape and a spherical shape. Then, the binding affinity for MDM2 becomes relatively high due to the addition of nutlin-3, which prevents the interaction between p53TAD and MDM2 and releases GST-p53TAD from MDM2, thereby converting the shape of MLP from a spherical shape to an open shape (tMLP) such as a dumbbell-like structure. As can be confirmed in FIG. 7B, since the translocation signature of a single molecule event reflects the shape of a protein, the nanopore signal of MLP is expected to have a single peak (type I) while the t-MLP, after the nutlin-3 addition, is expected to have a double peak signal (type II).

For the nanopore experiment, both cis- and trans-chambers were filled with 1 M KCl of 1×PBS buffer (pH=7.4) and a potential of 200 mV was applied through a membrane, and thereby the negatively charged MLP was drawn toward the direction of the nanopores. The protein samples were prepared by incubating along with nutlin-3 at a molar ratio exceeding the MLP protein, and in particular, the molar ratio between MLP and nutlin-3 was 0-fold (free MLP), 1-fold (1:1), 5-fold (1:5), and 10-fold (1:10).

FIG. 8A shows a typical I-V curve of nanopores and FIG. 8B shows the detection results of translocation signals after the addition of each protein sample (100 nM). FIGS. 8D to 8G show the linked events of translocation of MLPs that pass through nanopores when the nutlin-3 concentration is 1:0, 1:1, 1:5, and 1:10. As a result, a protein sample without nutlin-3 showed a single peak (type I) signal (FIG. 8D). From the above result, it was confirmed that a structure with a single spherical shape could be formed by the interaction between p53TAD and MDM2. In contrast, protein samples where the molar ratio between nutlin-3 and MLP was 1:1 showed not only a single peak signal but also a double peak signal (type II). Further, the statistical information on MLP and tMLP that are affected by nutlin-3 can be obtained by counting type II signals relative to the entire translocation signals. As such, the method for collecting statistical information is significantly different from other methods which rely on ensemble approaches. As a result, as can be confirmed in FIG. 8C, the fractions of type II signals among all of the events are 9.3% (1:1), 12.0% (1:5), and 23.0% (1:10).

Considering the dissociation coefficient ($K_d$=about 600 nM) of p53TAD and MDM2 and the dissociation coefficient ($K_d$=about 100 nM) of nutlin-3 and MDM2, the fractions of type II signals for each molar ratio between nutlin-3 and MLP were shown to be slightly smaller than expected. One reason for this is that the samples were not processed to ensure all of the possible interactions between nutlin-3 and MDM2. For example, for the interaction between nutlin-3 and MDM2t, the original interaction between p53TAD and MDM2 must first be dissociated, and this dissociation process may be a bottleneck process for the complete reaction between nutlin-3 and MDM2. Another reason is that the dissociation coefficient ($K_d$) of the linking structure between p53TAD and MDM2 can vary compared to the reported value due to the change in the spatial proximity between p53TAD and MDM2.

Other diffusion rates of proteins may cause protein molecules to approach the pore entrances at different rates. Specifically, in the solid-state nanopore experiment, biomolecules move through nanopores by an applied electric field. Since most of the electric field is applied near the entrance of each nanopore, biomolecules must approach the pore entrances through random movement, and the electrophoresis rate overwhelms the diffusion rate of the proteins at each nanopore entrance and moves through the nanopore by electrophoresis. Accordingly, structural changes in proteins can result in large differences in diffusivity. The estimated bulk diffusion coefficient ($D_{0,MLP}$) for MLP is calculated to be 68.05 nm$^2$ μs$^{-1}$ while $D_0$ ($D_{0,tMLP}$) for tMLP is calculated to be 45.40 nm$^2$ μs$^{-1}$, which is lower than that for MLP. To this end, tMLP is estimated to be in the form of a dumbbell, and as described above, the low $D_0$ of tMLP may affect the frequency of translocation events. As another possibility, some type II signals may have appeared as type I signals due to the insufficient temporal resolution of the detection system.

FIGS. 9A to 9D show scatter plots of mean values and dwell time of the normalized current blockade ($\Delta I/I_0$) of MLPs with or without nutlin-3 in different ratios between nutlin-3 and MLP. As a result, the sample without nutlin-3 showed only type I signals (FIG. 9A); however, the sample showed both type I and type II signals as the molar ratio between nutlin-3 and MLP increased (FIGS. 9B to 9D). This data apparently shows that the difference of $\Delta I/I_0$ between the two signals is not significant. However, type II signals appeared in a longer range of stop time compared to type I signals. These results indicate that the morphological changes in protein shapes do not induce a pure change in protein volumes, but induce only the structural changes that affect the translocation through nanopores.

Experimental Example 5: Confirmation of Inhibition of MDM2-Linker-p53TAD (MLP) Binding Using NMR To confirm the effect of the method for screening protein-protein interaction inhibitors using the nanopores of the present invention, experiments were performed on protein-protein interactions between MDM2 and p53TAD and the inhibition by small molecules in an MLP single fusion protein frame by NMR.

Specifically, the 2D $^{15}$N-$^1$H heteronuclear single quantum correlation (HSQC) of $^{15}$N-labeled MLP spectra were in the presence or absence of nutlin-3. As a result, as can be confirmed in FIG. 10, the 2D HSQC mainly showed $^{15}$N-$^1$H cross-peaks in the p53TAD region of MLP. Unlike p53TAD alone, the $^{15}$N-$^1$H cross-peaks from the MDM2-binding residues (p53TAD residues 15 to 29) present in the p53TAD region of MLP were not observed, and this is due to the severe line-broadening by MDM2-binding. That is, such a line-broadening of cross-peaks indicates that MLP maintains a protein-protein interaction between MDM2 and p53TAD. On the contrary, a distinct recovery of some NMR cross-peaks of MLP was discovered after the addition of nutlin-3. NMR resonance designation shows that the recovered residues (residues 18, 20, 23, 28, and 29) are mainly located in the MDM2-binding region of p53TAD in the MLP, and nutlin-3 prevents the protein-protein interaction between MDM2 and p53TAD, thereby inducing a structural change in the MLP.

Experimental Example 6: Analysis of Dynamics of Protein Translocation of MDM2-Linker-p53TAD (MLP) and Protein Size Using Nanopores Histograms on dwell time are results derived from scatter plots and they are shown in FIGS. 9E to 9F. The distribution of type II events in all of the nutlin-3 concentrations clearly shows that tMLP is slowly translocated through nanopores. For the quantitative evaluation of translocation behaviors of MLP and tMLP, the 1D diffusion drift model proposed by Ling et al. was used.

$$F(t) = \frac{h_{eff}}{\sqrt{4\pi D_p t^3}} e^{-\frac{(h_{eff} - v_d t)^2}{4 D_p t}} \quad \text{[Equation 1]}$$

In Equation 1 above, F(t) represents a probability density function, $h_{eff}$ represents an effective thickness of pore, $D_p$ represents a protein diffusion coefficient inside of a pore, and $v_d$ represents a drifting speed of a protein. The histograms on dwell time were fitted to Equation 1, and thereby the free parameters with regard to type I and type II events (i.e., $D_p$ and $v_d$) were extracted ($R^2 > 0.96$).

The $D_p$ values obtained with regard to type I events in each of free, 1:1, 1:5, and 1:10 were 4.92±0.10 nm$^2$ μs$^{-1}$, 5.05±0.13 nm$^2$ μs$^{-1}$, 4.57±0.10 nm$^2$ μs$^{-1}$, and 5.19±0.09 nm$^2$ μs$^{-1}$. In contrast, the $D_p$ values obtained with regard to type II events in each of 1:1, 1:5, and 1:10 were much lower: 0.29±0.02 nm$^2$ μs$^{-1}$, 0.33±0.01 nm$^2$ μs$^{-1}$, and 0.37±0.02 nm$^2$ μs$^{-1}$. In addition, the low $v_d$ values obtained with regard to type II events in each of 1:1, 1:5, and 1:10 were 0.71±0.01 nm s$^{-1}$, 0.66±0.01 nm μs$^{-1}$, and 0.79±0.01 nm μs$^{-1}$, whereas the low $v_d$ values obtained with regard to type I events in each of 1:1, 1:5, and 1:10 were 1.48±0.04 nm μs$^{-1}$, 1.46±0.02 nm μs$^{+1}$, and 1.44±0.04 nm μs$^{-1}$ (in the case of free: 1.46±0.02 nm s$^{-1}$).

Similar $D_p$ and $v_d$ values obtained with regard to each of the nutlin-3 concentrations represent the same structure for MLP and tMLP. On the other hand, the low $D_p$ and $v_d$ values were obtained with regard to type II events, and this indicates that MLP structures are changed to a state to be slower and less diffused within the nanopores. Comparing the $D_p$ values with bulk diffusion coefficient, the $D_p$ value for MLP is about 14-fold smaller than $D_0$, and this indicates that the MLP diffusion movement is seriously delayed within the nanopores. In contrast, the $D_p$ value for tMLP is about 137-fold smaller than $D_{0,tMLP}$, and this is thought to reflect the spatial confinement not only in the nanopores but also in the protein-pore interaction.

FIG. 10 shows histograms of the fractional current with regard to type II intra-peaks. Since GST-p53TAD, MDM2, and amino acid linkers represent different volumes, 3 different current drops were measured within type II events.

The information on the internal peaks of signals are each defined as $I_H$, $I_M$, and $I_L$, for high, middle, and low levels of fractional current (FIG. 10A). The average fractional current $\langle I_H \rangle$ represents about 0.071, about 0.077, and about 0.068 for 1:1, 1:5, and 1:10, respectively. The $\langle I_M \rangle$ value represents about 0.044, about 0.045, and about 0.044 for 1:1, 1:5, and 1:10, respectively, thus being smaller than the $\langle I_H \rangle$ values. The present inventors have discovered the average $\langle I_L \rangle$ values which are structurally reflected by amino acid linkers, and they are 0.020, 0.019, and 0.022 for 1:1, 1:5, and 1:10, respectively. Each of the $\langle I_H \rangle$, $\langle I_M \rangle$, and $\langle I_L \rangle$ values is consistent in all of the nutlin-3 concentration conditions, and these represent the same signal.

Since the structure of the protein complex used in the experiment can be divided into three parts, it was assumed that $I_H$, $I_M$, and $I_L$ represent GST-p53TAD, MDM2, and amino acid linkers, respectively. Based on the above values, the hydrodynamic diameters of the proteins were estimated using an analytical solution.

$$d_m = \left[ \left( \frac{\Delta I}{I_0} \right)(h_{\mathit{eff}} + 0.8 d_p) d_p^2 \right]^{1/3} \quad \text{[Equation 2]}$$

In Equation 2 above, $d_m$ represents diameter of a protein, $h_{\mathit{eff}}$ represents an effective thickness of a pore (7 nm), and $d_p$ represents a diameter of a pore (8 nm). With respect to $I_H$ and $I_M$, data calculated that $d_m = 4.07 \pm 0.81$ nm and $3.49 \pm 1.10$ nm, respectively. Comparing to the experimental results, the X-ray crystal structures of GST-p53TAD and MDM2 were cited from Protein Data Bank (PDB code: 1BG5; GST-p53TAD, 1YCR; and MDM2).

The estimated physical dimensions of the crystal structures of GST-p53TAD and MDM2 are $4.7 \times 5.3 \times 6.0$ nm$^3$ and $2.4 \times 2.6 \times 4.1$ nm$^3$, respectively. Considering that crystallized protein samples in X-ray diffraction measurements have a neighboring environment significantly different from an aqueous solution, the nanopore results reflect the size of other proteins well.

While GST-p53TAD and MDM2 are assumed to have a spherical structure, the amino acid linker was assumed to have a cylindrical structure. If the amino acid linker is taken as a cylinder with a membrane thickness, the estimated diameter of the cylinder is $2.72 \pm 1.47$ nm. This result is about 5 times larger than the reported result. Although it has not been clearly confirmed, the linker would not have fully extended while passing through nanopores. Additionally, due to the rapid rate of translocation, it is possible that the $I_L$ located between the internal peaks of GST-p53TAD and MDM2 may have not been sufficiently analyzed.

Those of ordinary skill in the art will recognize that the present invention may be embodied in other specific forms without departing from its spirit or essential characteristics. In this regard, the described embodiments are to be considered in all respects only as illustrative and not restrictive. The scope of the present invention is therefore indicated by the appended claims rather than by the foregoing description. All changes which come within the meaning and range of equivalency of the claims are to be embraced within the scope of the present invention.

[National R&D Business Supporting this Invention]
[Reference No. for the Project] NRF-2012M3C1A3671508
[Government Department] The Ministry of Science, ICT and Future Planning (MSIP)
[National R&D Management Agency] The National Research Foundation of Korea, (NRF)
[Name of Research Business] Pioneer Research Center Program
[Name of Research Project] Design of protein-based biocontents and technology development for nanopore application
[Agency in charge] Korea Research Institute of Bioscience and Biotechnology (KRIBB)
[Research Period] Sep. 1, 2012 to Feb. 28, 2018
[National R&D Business Supporting this Invention]
[Reference No. for the Project] NRF-2017R1E1A1A01074403
[Government Department] The Ministry of Science and ICT (MSIT)
[National R&D Management Agency] The National Research Foundation of Korea (NRF)
[Name of Research Business] Strategic Project of Basic Research Business in Science and Engineering Field
[Name of Research Project] Development of IoT nanopore sensor technology for point-of-care diagnosis of highly pathogenic infectious disease)
[Agency in charge] Korea Research Institute of Bioscience and Biotechnology (KRIBB)
[Research Period] Nov. 1, 2017 to Oct. 31, 2022

The invention claimed is:

1. A method of screening for protein-protein interaction inhibitors to identify therapeutic drug candidates for treating a disease using a solid-state nanopore, comprising:
    (a) forming a protein complex associated with the disease in which a first protein and a second protein are bound together by a protein-protein interaction;
    (b) measuring the intensity or frequency of an electrical signal generated while the protein complex passes through the nanopore; and
    (c) treating the protein complex with a candidate protein-protein interaction inhibitor, and measuring the intensity or frequency of an electrical signal generated while the protein complex passes through the nanopore, wherein the candidate protein-protein interaction inhibitor is identified as a therapeutic drug candidate for treating the disease when the candidate inhibitor specifically inhibits the protein-protein interaction based on measuring the intensity or frequency of the electrical signal in step (c).

2. A method of screening for protein-protein interaction inhibitors to identify therapeutic drug candidates for treating a disease using a nanopore, comprising:
    (a) forming a protein complex associated with the disease in which a first protein and a second protein are bound together by a protein-protein interaction;
    (b) measuring the intensity or frequency of an electrical signal generated while the protein complex passes through the nanopore; and
    (c) treating the protein complex with a candidate protein-protein interaction inhibitor, and measuring the intensity or frequency of an electrical signal generated while the protein complex passes through the nanopore, wherein the candidate protein-protein interaction inhibitor is identified as a therapeutic drug candidate for treating the disease when the candidate inhibitor specifically inhibits the protein-protein interaction based on measuring the intensity or frequency of the electrical signal in step (c), wherein in the protein complex formed in step (a), the first protein and the second protein are linked by a linker.

3. The method of claim 1, wherein the electrical signal to be measured is the intensity or frequency of the electrical signal generated while the protein complex passes through the solid-state nanopore, and the method further comprises:
   (d) comparing the electrical signals measured in steps (b) and (c), and determining the candidate protein-protein interaction inhibitor is a therapeutic drug candidate when there is a change in the intensity or frequency between the two signals measured.

4. The method of claim 2, wherein the electrical signal to be measured is the pattern of the electrical signal generated while the protein complex passes through the nanopore, and
   the method further comprises determining the candidate protein-protein interaction inhibitor is a therapeutic drug candidate when the measured pattern shows multiple peaks.

5. The method of claim 1, wherein in step (a), the first protein is mouse double minute 2 (MDM2) and the second protein is p53; or the first protein is p53 and the second protein is MDM2.

6. The method of claim 2, wherein the linker consists of 10 to 30 amino acids.

7. A method of screening for protein-protein interaction inhibitors to identify therapeutic drug candidates for treating a disease using a nanopore, comprising
   (a) attaching to a first protein or to a second protein, a third protein as a tag which when bound to the first protein or to the second protein does not cause any significant change in the net charge of the first or the second protein to which it is attached but increases the measurement sensitivity of the nanopore, wherein a protein complex between the first protein and the second protein is associated with the disease
   (b) forming a protein complex in which the first protein and the second protein are bound together by a protein-protein interaction;
   (c) measuring the intensity or frequency of an electrical signal generated while the protein complex passes through the nanopore; and
   (d) treating the protein complex with a candidate protein-protein interaction inhibitor, and measuring the intensity or frequency of an electrical signal generated while the protein complex passes through the nanopore, wherein the candidate protein-protein interaction inhibitor is identified as a therapeutic drug candidate for treating the disease when the candidate inhibitor specifically inhibits the protein-protein interaction based on measuring the intensity or frequency of the electrical signal in step (c).

8. The method of claim 7, wherein the third protein is a tag selected from the group of typical globular proteins consisting of glutathione S-transferase (GST), maltose binding protein (MBP), thioredoxin (TRX), green fluorescent protein (GFP), and chitin binding protein (CBD).

9. The method of claim 1, wherein the protein-protein interaction inhibitor is a therapeutic drug candidate for a disease selected from the group consisting of cancers, degenerative diseases, metabolic diseases, cranial nerve diseases, cardiovascular diseases, microbial infectious diseases, and immune diseases.

10. A method for analyzing a protein-protein interaction using a nanopore, comprising: (a) preparing a linked protein where a first protein and a second protein are fused via a linker; (b) measuring the intensity or frequency of an electrical signal generated while the linked protein passes through the nanopore; (c) analyzing the pattern of electrical signals generated in step (b) so as to analyze the protein-protein interaction, wherein the method for analyzing a protein-protein interaction comprises: determining that the protein-protein interaction is formed between the first protein and the second protein when the electrical signal by the first protein and the second protein linked by a linker shows a single peak; and determining that a protein-protein interaction is not formed between the first protein and the second protein when the electrical signal by the first protein and the second protein linked by a linker shows multiple peaks.

11. The method of claim 10, wherein the linker consists of 10 to 30 amino acids.

\* \* \* \* \*